(12) United States Patent
Chana

(10) Patent No.: US 10,987,115 B2
(45) Date of Patent: Apr. 27, 2021

(54) APPARATUS FOR USE IN SURGERY

(71) Applicant: Gursharan Singh Chana, Sutton Coldfield (GB)

(72) Inventor: Gursharan Singh Chana, Sutton Coldfield (GB)

( * ) Notice: Subject to any disclaimer, the term of this patent is extended or adjusted under 35 U.S.C. 154(b) by 314 days.

(21) Appl. No.: 15/754,181

(22) PCT Filed: Aug. 22, 2016

(86) PCT No.: PCT/GB2016/052594
§ 371 (c)(1),
(2) Date: Feb. 21, 2018

(87) PCT Pub. No.: WO2017/032993
PCT Pub. Date: Mar. 2, 2017

(65) Prior Publication Data
US 2018/0250021 A1    Sep. 6, 2018

Related U.S. Application Data

(60) Provisional application No. 62/207,957, filed on Aug. 21, 2015.

(51) Int. Cl.
*A61B 17/17* (2006.01)
*A61F 2/46* (2006.01)
*A61F 2/30* (2006.01)

(52) U.S. Cl.
CPC .......... *A61B 17/175* (2013.01); *A61F 2/4607* (2013.01); *A61F 2002/30553* (2013.01); *A61F 2002/4619* (2013.01)

(58) Field of Classification Search
CPC .. A61B 17/1742; A61B 17/175; A61F 2/4607
See application file for complete search history.

(56) References Cited

U.S. PATENT DOCUMENTS

2014/0135781 A1* 5/2014 Chana ................ A61B 17/1739
606/96
2015/0057666 A1   2/2015 Kelley

FOREIGN PATENT DOCUMENTS

WO   2011/045568   4/2011
WO   2012/006508   1/2012

OTHER PUBLICATIONS

International Search Report and Written Opinion for PCT/GB2016/052594 dated Dec. 20, 2016, 11 pages.

* cited by examiner

*Primary Examiner* — Olivia C Chang
(74) *Attorney, Agent, or Firm* — Myers Bigel, P.A.

(57) ABSTRACT

A targeting kit comprises (i) a mounting arrangement for releasably mounting the targeting kit on an implant, (ii) first and second guide members having an elongate shape with a bore running along its longitudinal axis (iii) a holding arrangement for holding the first and second guide members, the holding arrangement being adjustable between a release condition, in which the positions of the first and second guide members are adjustable, and a holding condition, in which the first and second guide members are in a fixed position, and (iv) a bridging arrangement between the mounting arrangement and the first and second guide members, to space the first and second guide members with respect to the mounting arrangement, the bridging arrangement being adjustable between a release condition, in which the position of the mounting arrangement is adjustable, and a holding condition, in which the first and second guide members are fixedly spaced.

19 Claims, 20 Drawing Sheets

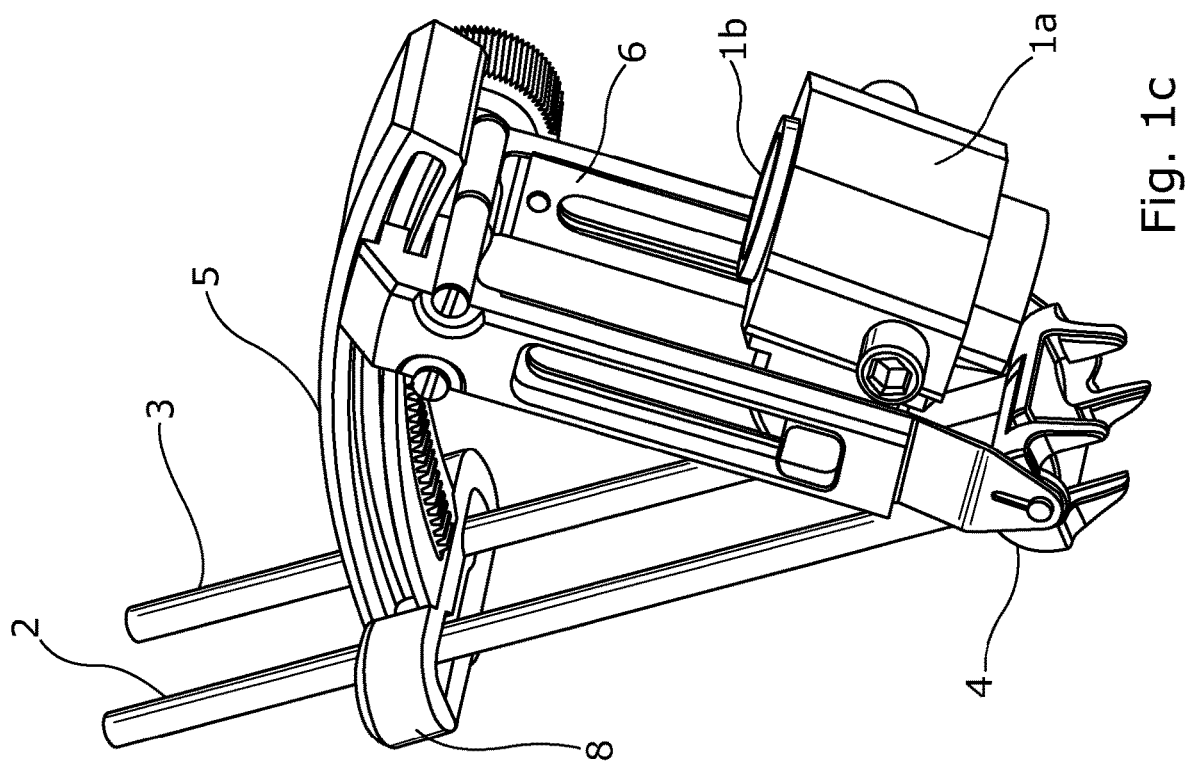
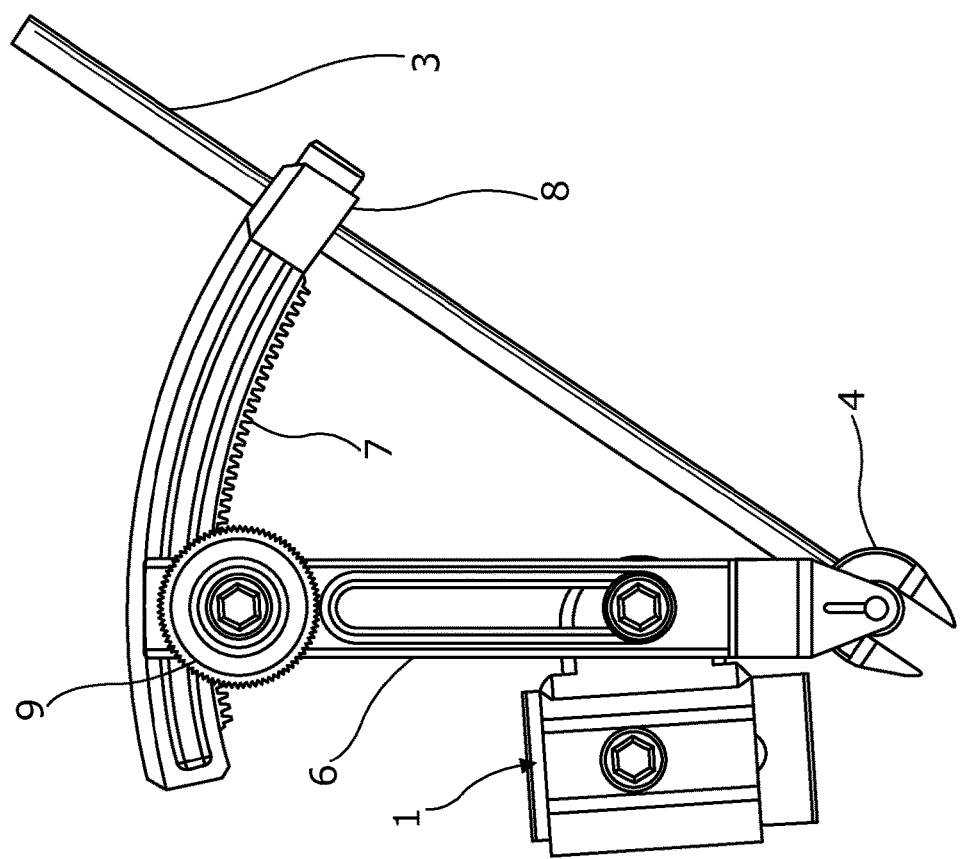

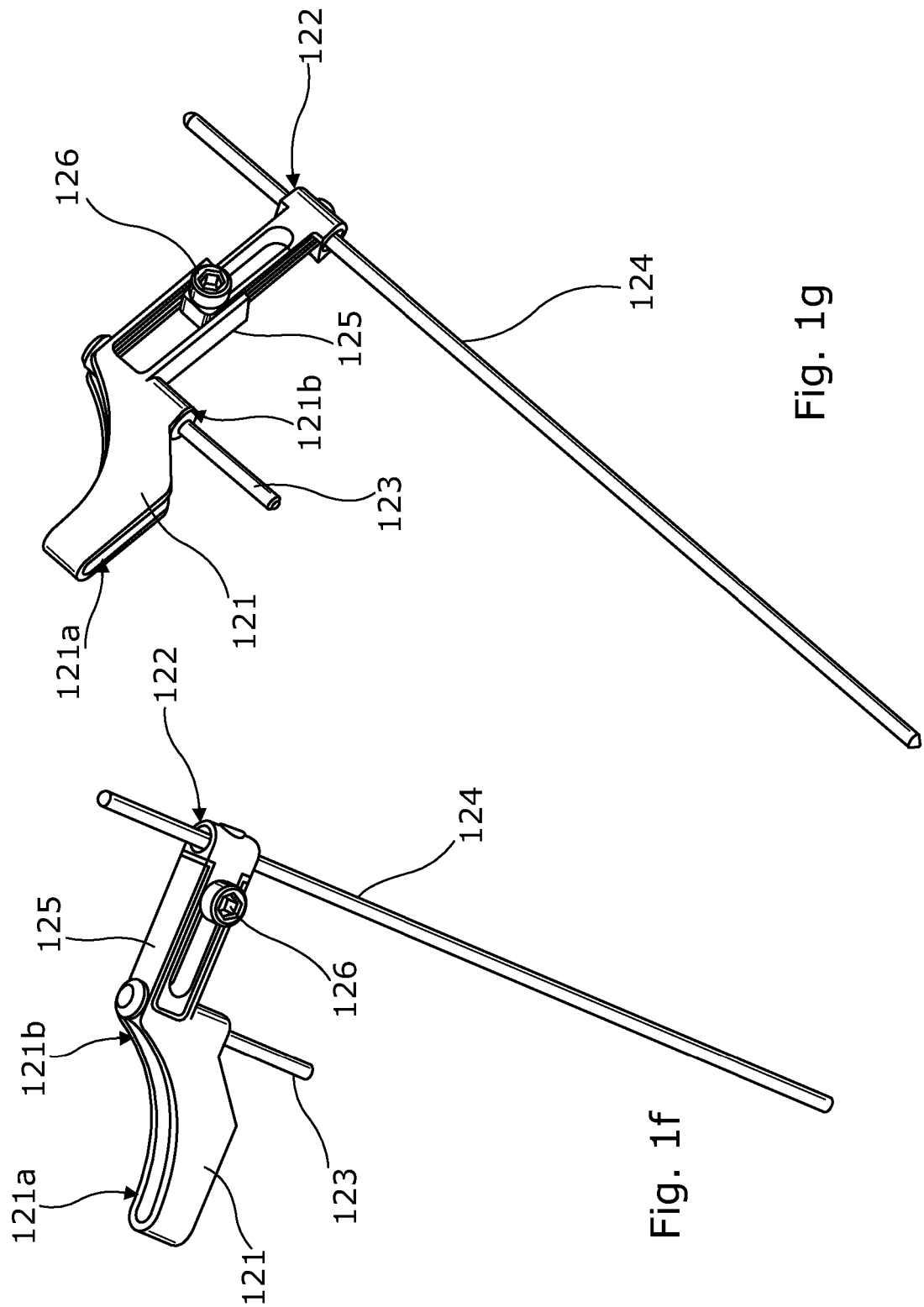

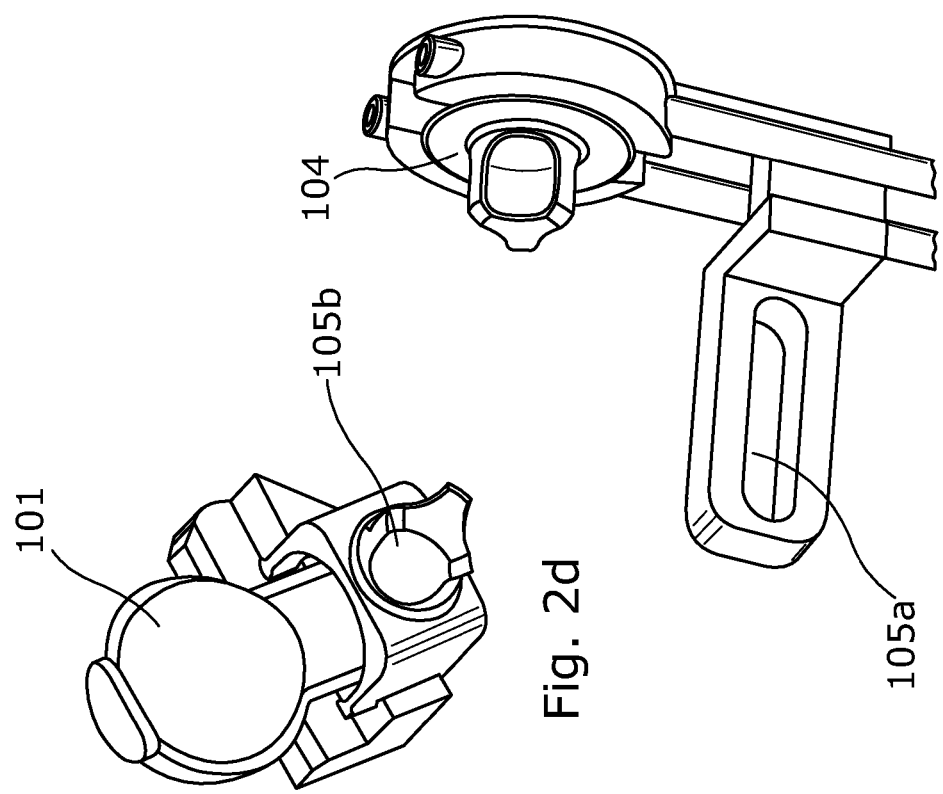
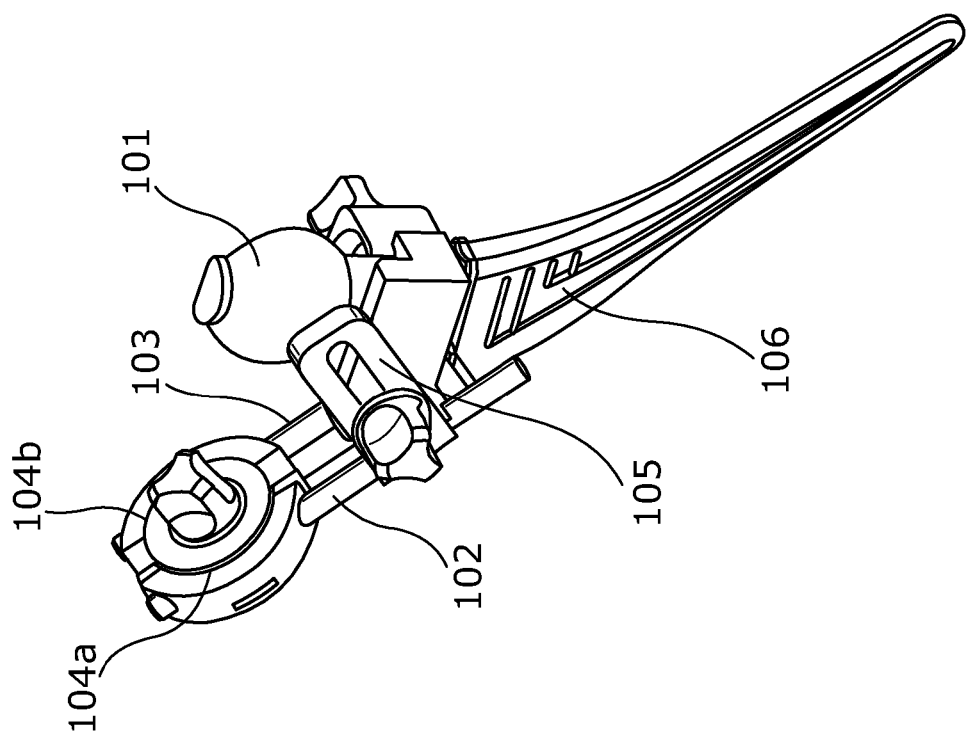

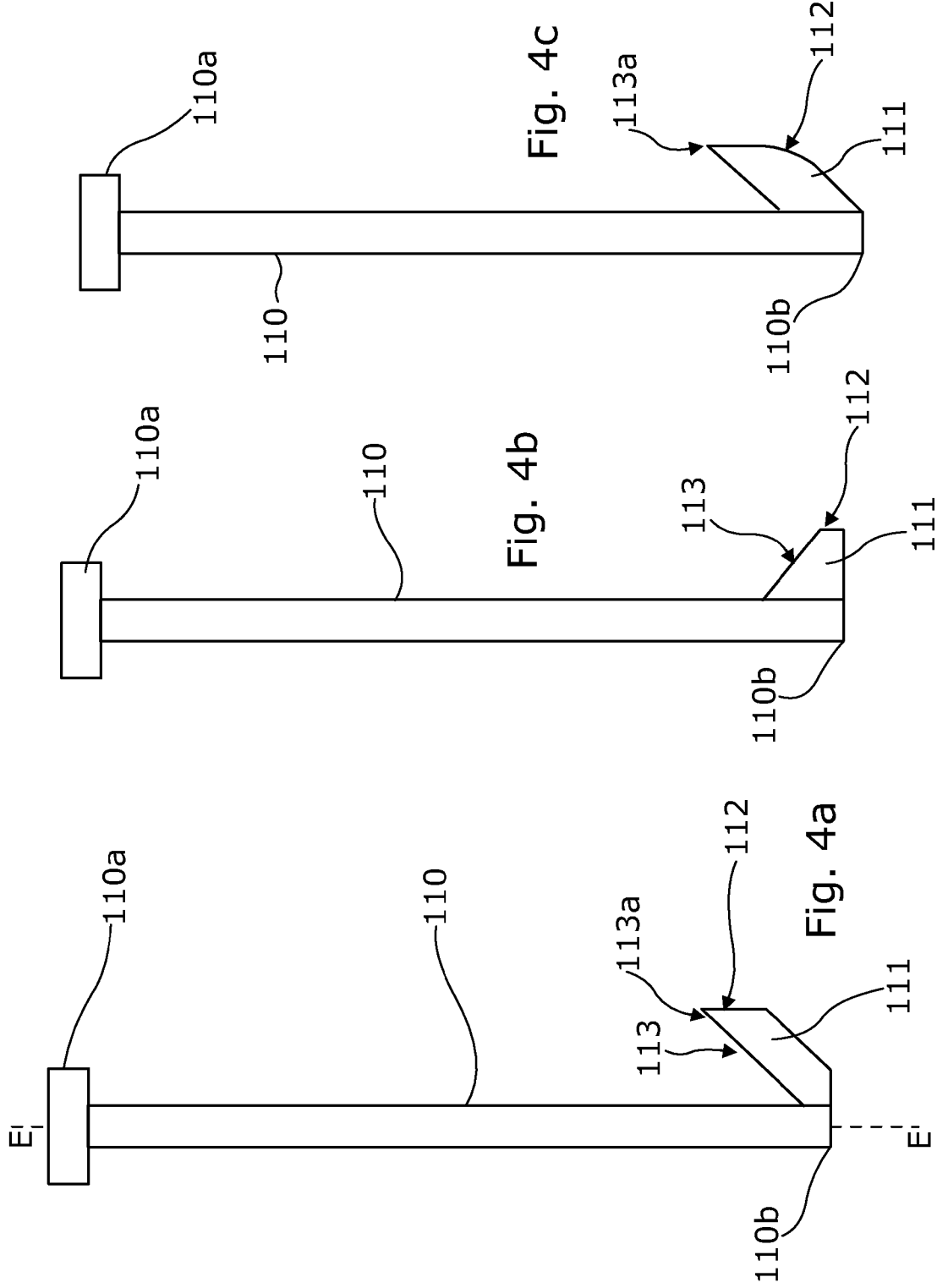

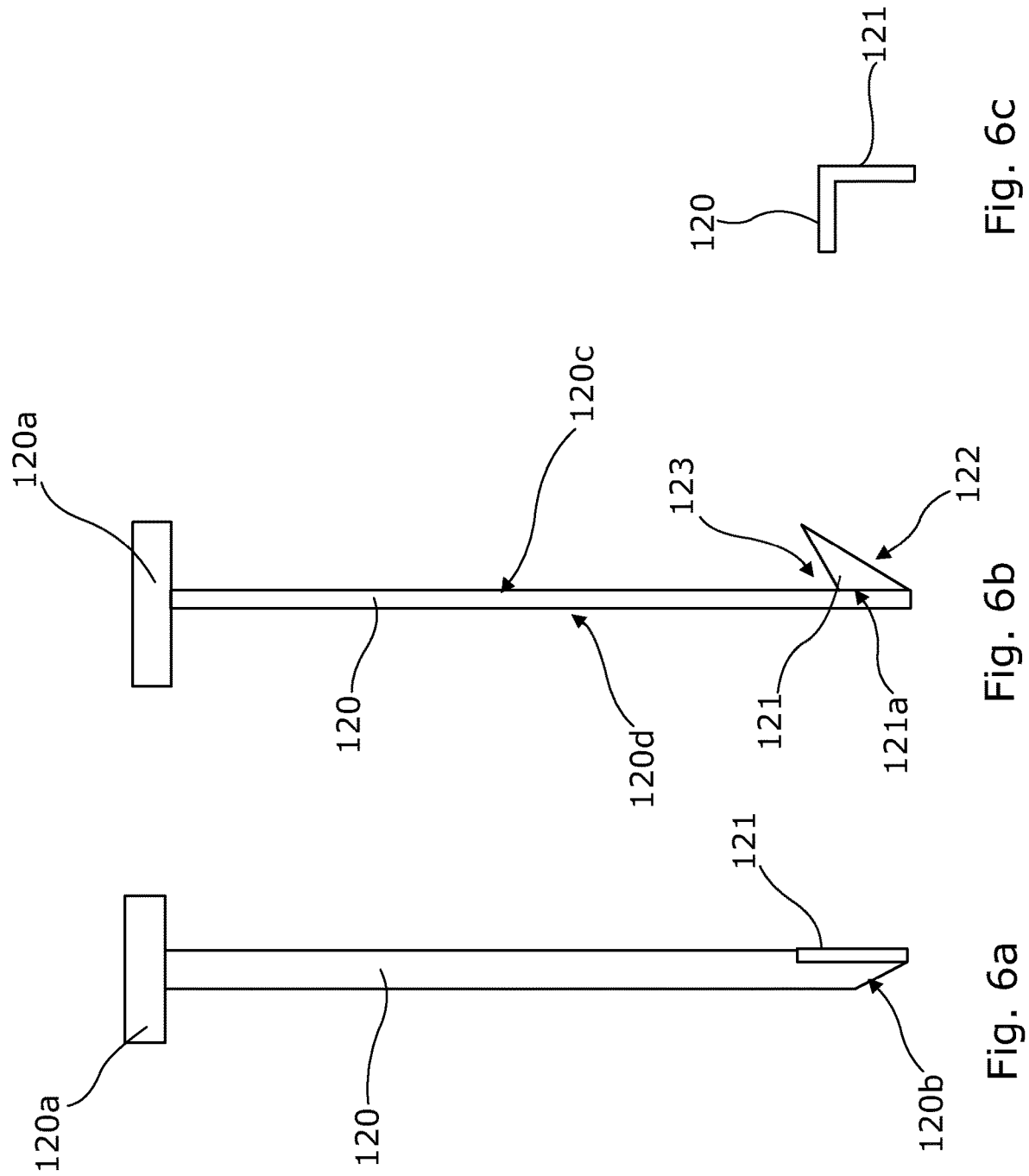

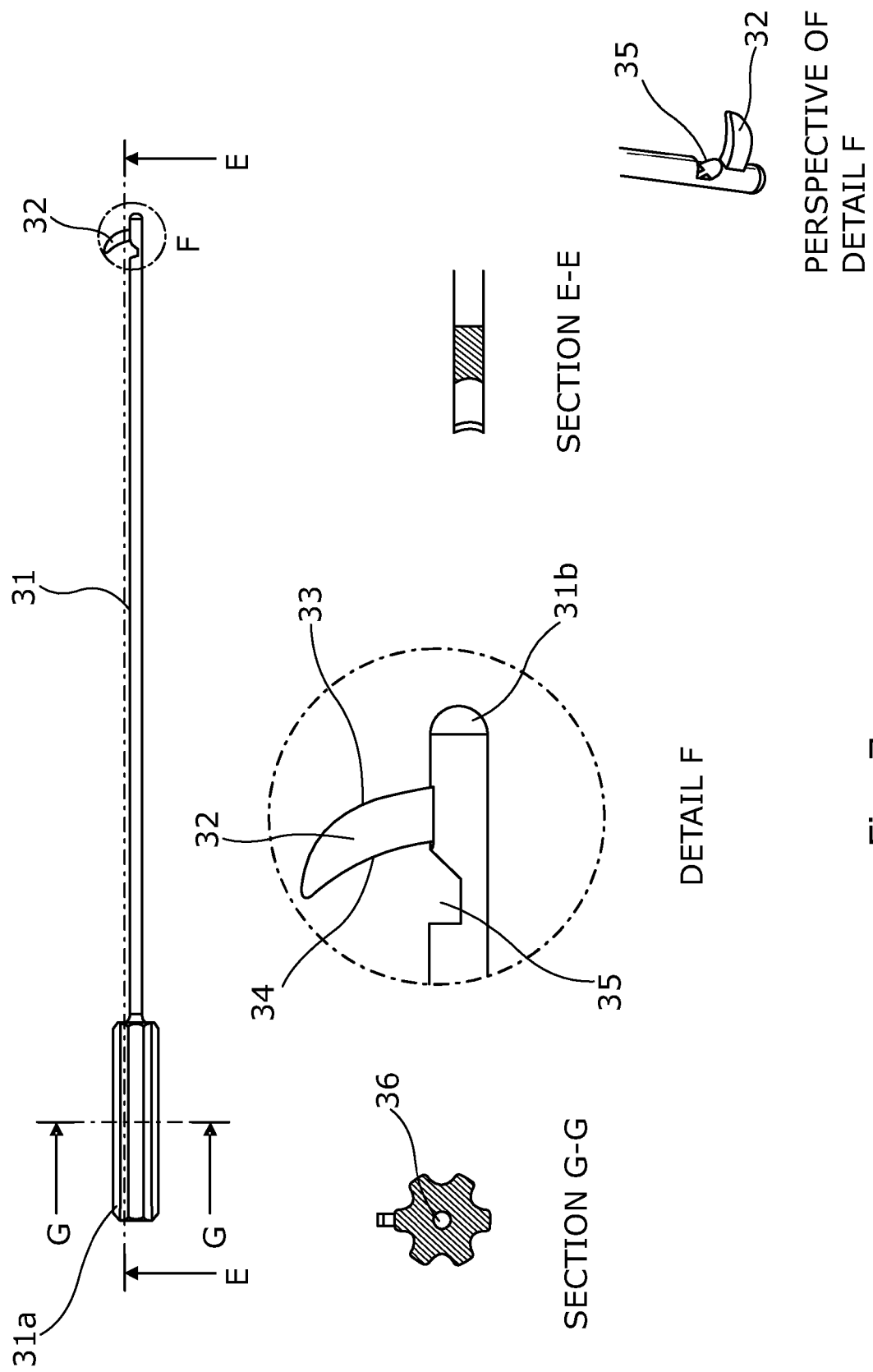

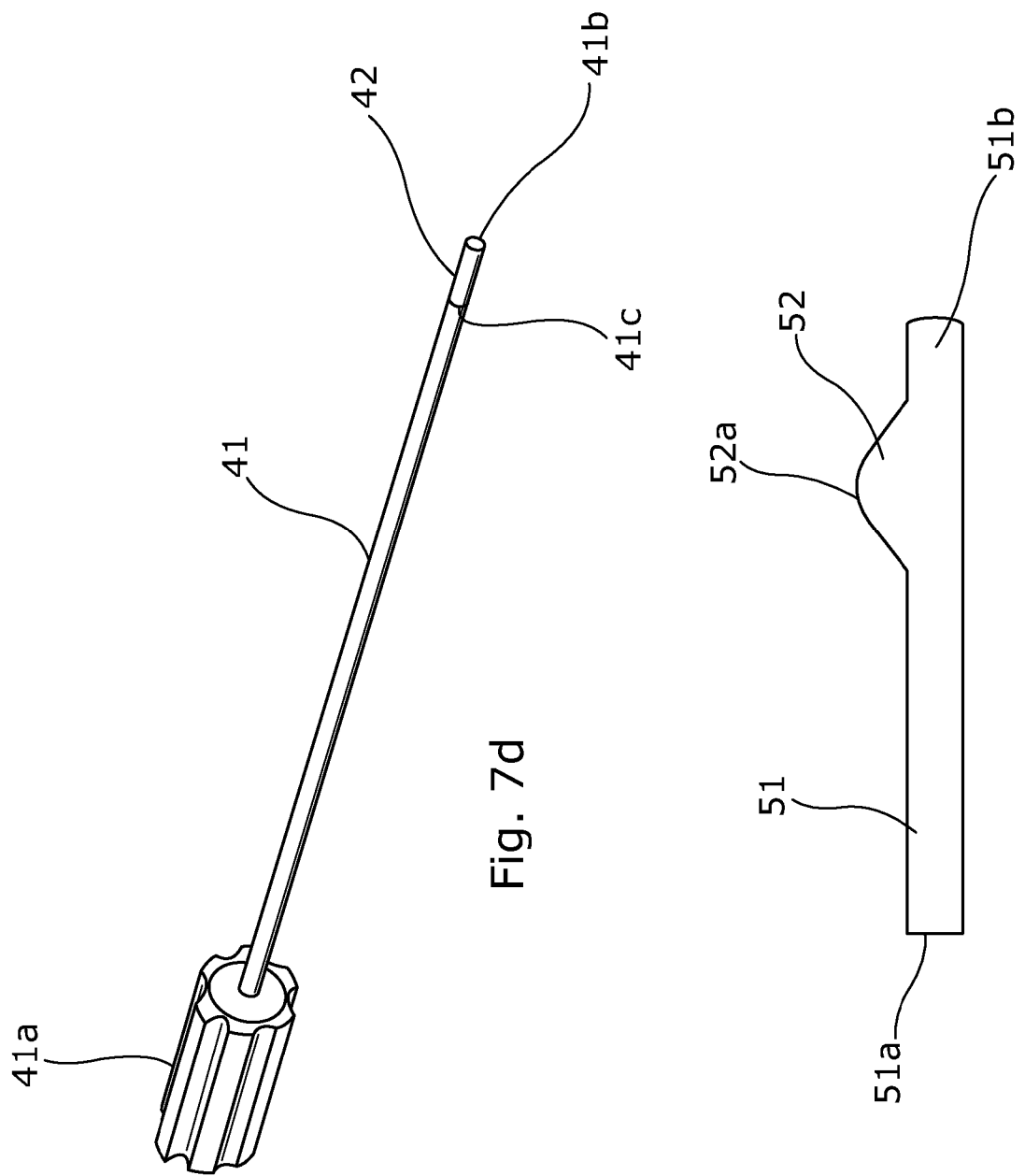

APPARATUS FOR USE IN SURGERY

RELATED APPLICATIONS

The present application is a 35 U.S.C. § 371 national phase application of PCT International Application No. PCT/GB2016/052594, filed Aug. 22, 2016, which claims priority from U.S. Provisional Patent Application No. 62/207,957 filed Aug. 21, 2015, the disclosures of which are hereby incorporated herein by reference in their entirety.

This invention relates to methods of removing implants embedded in surrounding tissue material and to associated apparatus for use in removing implants. More particularly, this invention relates to methods and apparatus for removing implants, such as femoral implants, from surrounding tissue material, e.g. in a human or animal body.

DESCRIPTION OF THE PRIOR ART

It is often necessary to remove implants that have previously been inserted, for example, where the implant has become loose, or the tissue surrounding the implant is infected. The failure rate of femoral implants, necessitating removal and insertion of a new implant, is believed to be about 10%.

Implants may generally be cemented or uncemented into position. For uncemented implants bony ingrowth is encouraged, which serves to secure the implant. Fibrous tissue may grow and encapsulate the implant.

A disadvantage of many known approaches is that to remove the implant any cement and bony ingrowth around the implant needs to be removed. In practice this results in large amounts of surrounding tissue (e.g. bone) being taken out, with a significantly larger cavity being left behind. The surgery is therefore relatively invasive and more expensive. In addition, the recovery from the surgery takes longer, and the patient cannot load bear through the new implant for some time after the surgery.

Common approaches to removing implants involve the use of standard osteotome devices.

The present invention provides an approach, and associated apparatus, to remove uncemented implants that have previously been inserted in a human or animal body.

SUMMARY OF THE INVENTION

The present invention permits an implant, especially a femoral implant, to be more readily removed from the surrounding tissue and with significantly less loss of tissue around the implant. The procedure is less invasive and generally will involve loss of tissue around the implant of the order of only about 0.6 mm, or even less, in each direction.

As the skilled reader will appreciate, a femoral implant has a tapered body. This extends from a broader proximal end, which provides a shoulder portion, to a narrower distal end. A neck extends from the proximal end, and a head extends from the neck.

The procedure generally involves firstly creating two access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant (e.g. at a distance of about 0.3 to 1.2 cm beyond the distal end, and preferably 0.5 to 1 cm beyond the distal end). The anterior access tunnel is spaced from and substantially parallel to the anterior surface of the implant and the posterior access tunnel is spaced from and substantially parallel to the posterior surface of the implant.

The anterior access tunnel is preferably spaced from the anterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm.

The posterior access tunnel is preferably spaced from the anterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm.

The access tunnels may suitably be elongate bores with round cross sections, e.g. substantially circular cross sections. The diameter of the access tunnels may suitably be from 0.5 mm to 5 mm, preferably from 1 mm to 4 mm, e.g. from 2 mm to 4 mm or from 2.5 mm to 3.5 mm.

This first step of the procedure is suitably effected using a targeting kit, which ensures the access tunnels are created at the required locations on the anterior and posterior of the implant. The access tunnels may be created using conventional tools, such as a drill and drill bits.

The targeting kit may, in one embodiment, be a drill guide of the type described in WO2011/045568. Such a drill guide is suitably secured on a projection of a femoral implant.

However, in a preferred embodiment, the targeting kit is a novel targeting kit according to the invention as claimed, which is suitable for being secured on the head or neck of a femoral implant.

This targeting kit of the invention comprises:
- a mounting arrangement for releasably mounting the targeting kit on the head or neck of a femoral implant,
- first and second guide members, each of which is an elongate shape with a bore running along its longitudinal axis, each guide member being able to receive a drill bit through its bore,
- a holding arrangement for holding the first and second guide members, the holding arrangement being adjustable between a release condition, in which the positions of the first and second guide members are adjustable relative to each other, and a holding condition, in which the first and second guide members are held by the holding arrangement in a fixed position relative to each other,
- a bridging arrangement between the mounting arrangement and the first and second guide members, to space the first and second guide members with respect to the mounting arrangement, with the bridging arrangement being adjustable between a release condition, in which the position of the mounting arrangement is adjustable relative to the first and second guide members, and a holding condition, in which the first and second guide members are fixedly spaced with respect to the mounting arrangement by the bridging arrangement, such that the mounting arrangement can be secured onto the head or neck of the implant, with the first and second guide members being located on the neck or shoulder of the implant, with the first guide member located at the anterior of the implant and the second guide member located at the posterior of the implant, the first guide member being angled such that its longitudinal axis is spaced from and substantially parallel to the anterior surface of the implant and the second guide member being angled such that its longitudinal axis is spaced from and substantially parallel to the posterior surface of the implant.

In a preferred embodiment, the procedure involves locating the targeting kit of the invention on the implant, with the mounting arrangement being secured onto the neck of the implant.

In this embodiment, the targeting kit of the invention suitably comprises:
- a mounting arrangement for releasably mounting the targeting kit on the neck of a femoral implant,
- first and second guide members, each of which is an elongate shape with a bore running along its longitudinal axis, each guide member being able to receive a drill bit through its bore,
- a holding arrangement for holding the first and second guide members, the holding arrangement being adjustable between a release condition, in which the positions of the first and second guide members are adjustable relative to each other, and a holding condition, in which the first and second guide members are held by the holding arrangement in a fixed position relative to each other,
- a bridging arrangement between the mounting arrangement and the first and second guide members, to space and angle the first and second guide members with respect to the mounting arrangement, with the bridging arrangement being adjustable between a release condition, in which the position of the mounting arrangement is adjustable relative to the first and second guide members, and a holding condition, in which the first and second guide members are fixedly spaced and angled with respect to the mounting arrangement by the bridging arrangement, such that the mounting arrangement can be secured onto the neck of the implant, with the first and second guide members being located on the shoulder of the implant, with the first guide member located at the anterior of the implant and the second guide member located at the posterior of the implant, the first guide member being angled such that its longitudinal axis is spaced from and substantially parallel to the anterior surface of the implant and the second guide member being angled such that its longitudinal axis is spaced from and substantially parallel to the posterior surface of the implant.

The method may suitably involve steps as follows.

A section of the body of the implant is exposed on the anterior surface of the implant and a section of the body of the implant is exposed on the posterior surface of the implant (e.g. a section having a length of from 0.5 to 5 cm, such as from 1 to 3 cm, or from 0.5 to 2 cm, on each surface may be exposed).

The location of the distal end of the implant is determined via x-ray. This can be carried out at this stage of the procedure, or may have been determined in advance.

The first and second guide members are then moved such that they are located on the shoulder of the implant, with the first guide member located at the anterior of the implant and the second guide member located at the posterior of the implant. The distance between the first and second guide members can be adjusted via the holding arrangement, so as to ensure that the guide members locate alongside the exposed anterior surface and posterior surface of the implant.

The first guide member is angled such that it points towards the location of the distal end of the implant, as determined via x-ray. Its longitudinal axis is spaced from and substantially parallel to the anterior surface of the implant.

The second guide member is angled such that it points towards the location of the distal end of the implant, as determined via x-ray. Its longitudinal axis is spaced from and substantially parallel to the posterior surface of the implant.

The angle of the first and second guide members can be adjusted via the bridging arrangement, so as to ensure that the guide members are each positioned at an angle directed towards the location of the distal end of the implant, as determined via x-ray.

The targeting kit will then have its components arranged in the required orientation such that the guide members are on the midpoint of the medial-lateral axis of the shoulder of the implant, and are pointing towards the midpoint of the medial-lateral axis of the implant.

The targeting kit is suitably used in combination with an extra medullary targeting device. This device can attach to the first guide member and the second guide member (in turn) to check their alignment, to check that the guide member in question is pointing to the distal tip of implant, as determined via x-ray.

The extra medullary targeting device comprises:
- a targeting kit interlocking portion,
- an extra medullary guidance portion, and
- a holding arrangement for holding and spacing the targeting kit interlocking portion and the extra medullary guidance portion,
- wherein the targeting kit interlocking portion comprises:
- a first guide member interlocking component, which comprises a bore within which the first guide member of the targeting kit can be received, and
- a second guide member interlocking component, which comprises a locking pin that can be received in the bore of the second guide member of the targeting kit, wherein the elongate axis of the locking pin is parallel to the longitudinal axis of the bore,
- wherein the extra medullary guidance portion comprises a bore within which a test pin having an elongate body can be received, wherein the length of the pin's elongate body is greater than the length of the bore, such that when the test pin is received within the bore, a portion of its elongate body extends out from the exit end of the bore,
- and wherein the holding arrangement holds the two portions fixedly relative to each other in terms of their angle, such that the bore of the first guide member interlocking component and the bore of the extra medullary guidance portion have their longitudinal axes aligned, such that these bores run parallel to each other, but the holding arrangement being adjustable in terms of the distance between the two portions, with this holding arrangement being adjustable between a release condition, in which the distance between the two portions is adjustable, and a holding condition, in which the distance between the two portions is fixed,
    - such that the bore of the first guide member interlocking component can receive the first guide member of the targeting kit, and the locking pin of the second guide member interlocking component can be received in the bore of the second guide member of the targeting kit and such that the test pin can be received within the bore of the extra medullary guidance portion,
    - such that the bore of the first guide member interlocking component is angularly aligned with the first guide member of the targeting kit, and such that the locking pin of the second guide member interlocking component is angularly aligned with the second guide member of the targeting kit and such that the test pin located in the bore of the extra medullary guidance portion is consequently also angularly aligned with the first and second guide members of the targeting kit, such that the alignment of the test pin can be checked, to ensure that it is pointing to the distal tip of implant, as determined via x-ray, or the middle of the medio-lateral diameter of the femur at the level of the distal tip of the implant.

It will be appreciated that if the test pin is pointing to the distal tip of implant, as determined via x-ray, or is in or the middle of the medio-lateral diameter of the femur at the level of the distal tip of the implant, then in turn the guide members of the targeting kit are aligned in that same direction. The test pin and the guide members of the targeting kit all lie in the saggital plane.

This extra medullary targeting device can therefore be used to double check the alignment of the guide members of the targeting kit before the tunnels are drilled.

In an alternate embodiment, the procedure involves providing a trial implant or rasp having the same dimensions as the implant to be removed, and locating the targeting kit of the invention on the trial implant or rasp, with the mounting arrangement secured onto the head of the trial implant or rasp, with the first and second guide members being located on the neck of the trial implant or rasp, with the first guide member located at the anterior of the trial implant or rasp and the second guide member located at the posterior of the trial implant or rasp, the first guide member being angled such that its longitudinal axis is spaced from and substantially parallel to the anterior surface of the trial implant or rasp and the second guide member being angled such that its longitudinal axis is spaced from and substantially parallel to the posterior surface of the trial implant or rasp. The targeting kit can then be released from the head of the trial implant or rasp. The targeting kit will then have its components arranged in the required orientation such that when the targeting kit is located on the implant, with the mounting arrangement secured onto the head of the implant, the guide members are in the required direction. Thus the guide members are placed on the midpoint of the medial-lateral axis of the shoulder of the implant, and pointing towards the midpoint of the medial-lateral axis of the implant.

Secondly, the procedure involves removing bony ingrowth located adjacent to the anterior access tunnel, and removing bony ingrowth located adjacent to the posterior access tunnel and the posterior surface of the implant. The intention of this step is to extend the width of the access tunnels, preferably so that their widths substantially correspond with the width of the implant. Therefore the anterior access tunnel is broadened in a plane that is substantially parallel to the anterior surface of the implant, and the posterior access tunnel is broadened in a plane that is substantially parallel to the posterior surface of the implant.

This second step of the procedure is suitably effected using an osteotome device.

The osteotome device may be a novel osteotome device according to the invention.

The osteotome device of the invention comprises:

an elongate body having a proximal end that is provided with a handle and a distal end that is blunt, wherein the elongate body includes a distal section extending from the distal end to a shoulder point, and an indented section extending from the shoulder point towards the proximal end, wherein the depth of the distal section is greater than the depth of the indented section and wherein the shoulder point is located closer to the distal end than the proximal end;

a cutting portion extending from the indented section of the elongate body, the cutting portion having a front face and a back face, the back face being attached to the indented section of the elongate body and the front face being located outwardly of the elongate body, wherein the distance between the back face and the front face is substantially the same as the difference in depth between the distal section and the indented section of the elongate body, and wherein the front face of the cutting portion is blunt but is connected to the back face by a first cutting side and a second cutting side;

such that the osteotome device can be located in an access tunnel and pushed in the direction of the distal end of the implant so as to cut away bony ingrowth with the first cutting side and the second cutting side.

It is preferred that more than one osteotome device is used in this stage. In particular, a plurality of osteotome devices may be provided, with each having a different width of cutting portion (distance between the first cutting side and a second cutting side). Therefore a first osteotome device may be provided that is slightly wider than the width of the access tunnel (e.g. 0.5 mm wider or more, or 1 mm wider or more, such as from 1 mm to 5 mm wider) and this is pushed in the direction of the distal end of the implant so as to cut away bony ingrowth with the first cutting side and the second cutting side. Then a further osteotome device may be provided that is slightly wider than the width of the now-widened access tunnel (e.g. 0.5 mm wider or more, or 1 mm wider or more, such as from 1 mm to 5 mm wider) and this is pushed in the direction of the distal end of the implant so as to cut away bony ingrowth with the first cutting side and the second cutting side. This step can be repeated as required for both tunnels until the anterior access tunnel has been widened as required in a direction parallel to the anterior surface of the implant and the posterior access tunnel has been widened as required in a direction parallel to the posterior surface of the implant, preferably so that the widths of the tunnels substantially correspond with the respective widths of the implant surfaces. The skilled reader will understand that the access tunnels may therefore end up not being of a consistent width following this stage, but rather may be wider at the access point than at the point in the surrounding tissue located beyond the distal end of the implant.

Thirdly, the procedure involves removing bony ingrowth located between the implant and the femur in the anterior aspect, and removing bony ingrowth located between the implant and the femur in the posterior aspect.

It will be appreciated that the use of the osteotomes clears a channel that has the shape corresponding to the osteotome cutting blade. The osteotome cutting blade will not extend so as to clear all bony ingrowth from between the implant and the femoral cortex. Instead, it will normally be the case that on both the anterior aspect and the posterior aspect there is bony ingrowth between the implant and the inner cortex of the femur.

Therefore the intention of this step is to further extend the width of the access tunnels. In this regard, the amount of bony ingrowth between the implant and the femur in the anterior aspect is reduced. In addition, the amount of bony ingrowth between the implant and the femur in the posterior aspect is reduced.

Preferably the width of the access tunnels is increased so that their widths extend to the surface of the femoral cortex.

Therefore the anterior access tunnel is broadened in a plane that is substantially parallel to the anterior surface of the implant, but in the region between the implant and the inner cortex of the femur. This can be in both medial and lateral directions. The posterior access tunnel is broadened in a plane that is substantially parallel to the posterior surface of the implant, but in the region between the implant and the inner cortex of the femur. This can be in both medial and lateral directions.

This third step of the procedure is suitably effected using a curette device.

The curette device may be a novel curette device according to the invention.

The curette device of the invention comprises:
an elongate body having a proximal end that is provided with a handle and having a distal end that is blunt;
a cutting portion extending outwardly from the elongate body and located at or near the distal end, the cutting portion having a blunt edge and a cutting edge, wherein the cutting edge is at an angle of from 30 to 150 degrees to the elongate axis of the elongate body and the blunt edge is substantially parallel to the elongate axis of the elongate body;
such that the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

The curette device is used in the anterior access tunnel, so that the tunnel is broadened in a plane that is substantially parallel to the anterior surface of the implant, but in the region between the implant and the inner cortex of the femur.

It will be appreciated that this process can be effected in both medial and lateral directions.

The curette device is also used in the posterior access tunnel, so that the tunnel is broadened in a plane that is substantially parallel to the posterior surface of the implant, but in the region between the implant and the inner cortex of the femur.

It will be appreciated that this process can be effected in both medial and lateral directions.

In each case, the device is sent down the access tunnel when substantially axially aligned with the tunnel, so that the cutting edge does not cut any surface as it is sent down the tunnel; then when the distal end of the device is located at or near the distal (closed) end of the access tunnel the device is angled, such that the cutting edge contacts the bony ingrowth, and then the device is withdrawn from the access tunnel whilst being retained in an angled position, such that as the device is withdrawn the cutting edge cuts away bony ingrowth.

In one embodiment the curette device is used more than once in each access tunnel in this stage. In this regard, it may be repeatedly sent down the access tunnel, then angled, and then withdrawn from the access tunnel whilst being retained in an angled position, such that as the device is withdrawn the cutting edge cuts away bony ingrowth. Each time the device is withdrawn the cutting edge is effectively scraping a layer of bony ingrowth, and so reduces the depth of bony ingrowth between the surface of the implant and the inner cortex of the femur. In one embodiment this is repeated until there is no bony ingrowth between the surface of the femoral implant and the femoral cortex.

It will be appreciated that this step can be repeated as required for both tunnels until the anterior access tunnel has been widened as required and the posterior access tunnel has been widened as required, preferably so that there is no bony ingrowth between the surface of the femoral implant and the femoral cortex in the posterior aspect and/or the anterior aspect.

Next, in a fourth step, the procedure involves removing bony ingrowth located at the distal end of the implant, to create a cavity at the distal end of the implant that extends in the medial and lateral directions. Preferably the cavity also extends the available space at the distal end in the anterior and posterior directions. In one embodiment, the cavity extends beyond the medial surface of the implant, e.g. by 1 mm or more, such as from 2 mm to 1.5 cm, preferably from 3 mm to 1 cm. In one embodiment, the cavity extends beyond the lateral surface of the implant, e.g. by 1 mm or more, such as from 2 mm to 1.5 cm, preferably from 3 mm to 1 cm. In one embodiment, the cavity extends beyond the anterior surface of the implant, e.g. by 1 mm or more, such as from 2 mm to 1.5 cm, preferably from 3 mm to 1 cm. In one embodiment, the cavity extends beyond the posterior surface of the implant, e.g. by 1 mm or more, such as from 2 mm to 1.5 cm, preferably from 3 mm to 1 cm.

This fourth step of the procedure is suitably effected using a medial-lateral cavity maker device. This may also be called a distal space maker.

The medial-lateral cavity maker device may be a novel medial-lateral cavity maker device according to the invention.

The medial-lateral cavity maker device of the invention comprises:
an elongate body having a proximal end that is provided with a handle and a distal end that is blunt;
a cutting portion extending outwardly from the elongate body, the cutting portion being located closer to the distal end of the elongate body than the proximal end of the elongate body, the cutting portion having a connecting end attached to the elongate body and a protruding end located away from the elongate body, the connecting end and the protruding end being connected by a first edge located towards the distal end of the elongate body and a second edge located towards the proximal end of the elongate body, wherein the first edge is blunt but the second edge is a cutting edge;
such that the medial-lateral cavity maker device can be located in an access tunnel and rotated when the cutting portion is located beyond the distal end of the implant, so as to cut away bony ingrowth with the second edge of the cutting portion at the distal end of the implant, to create a cavity at the distal end of the implant that extends in the medial and lateral directions.

The cutting portion suitably extends in a plane that lies on the edge of the elongate body. This allows the cutting portion to be positioned parallel to the surface of the implant when the cutting portion is in a part of the access tunnel that is alongside the implant, with the cutting portion only then being rotated once the cutting portion is located beyond the distal end of the implant. This reflects the fact that the access tunnel is only widened in the second step of the procedure in a direction parallel to the surface of the implant; the dimensions of the access tunnel in all other directions remain relatively small. Therefore the extending portion of the cavity maker device, namely the cutting portion, needs to be able to be positioned in that widened dimension of the access tunnel so that it can pass down to a location beyond the distal end of the implant.

It is preferred that more than one medial-lateral cavity maker device is used in this stage. In particular, a plurality of medial-lateral cavity maker devices may be provided, with each having a different width of cutting portion (distance between the elongate body and the outermost point of the second edge of the cutting portion). Therefore a first medial-lateral cavity maker device may be provided that has a cutting edge that is slightly wider than the radius of the distal end of the implant (e.g. 0.5 mm wider or more, or 1 mm wider or more, such as from 1 mm to 5 mm wider) and this is rotated once it is located beyond the distal end of the implant so as to cut away bony ingrowth to create a cavity at the distal end of the implant that extends in the medial and lateral directions with the cutting edge. Then a further medial-lateral cavity maker device may be provided that has a cutting edge that is slightly wider than the radius of the now-widened cavity (e.g. 0.5 mm wider or more, or 1 mm wider or more, such as from 1 mm to 5 mm wider) and this is rotated once it is located beyond the distal end of the implant so as to cut away bony ingrowth to create a larger cavity at the distal end of the implant that extends in the medial and lateral directions with the cutting edge. This step can be repeated as required until the cavity has been widened as required.

In a fifth stage, the procedure involves providing a wire to extend from a first access point at the proximal surface of the surrounding tissue to a second access point at the proximal surface of the surrounding tissue via the anterior access tunnel, the cavity at the distal end of the implant and the posterior access tunnel, the wire comprising a cutting portion that can be used to cut away bony ingrowth at the surface of the implant.

This fifth step of the procedure is suitably effected using a wire delivery device.

The wire delivery device may be a novel wire delivery device according to the invention.

The wire delivery device of the invention comprises:
an elongate body having a proximal end that is provided with a handle and a distal end that is blunt;
a wire guidance portion extending outwardly from the elongate body, the wire guidance portion being located closer to the distal end of the elongate body than the proximal end of the elongate body, the wire guidance portion having a connecting end attached to the elongate body and a protruding end located away from the elongate body, the connecting end and the protruding end being connected by a first curved surface and a second curved surface, the first curved surface being convex and being located towards the distal end of the elongate body and the second curved surface being concave and being located towards the proximal end of the elongate body, wherein both the first curved surface and the second curved surface are blunt;
the elongate body having a bore running from its proximal end to an exit hole located adjacent to the second curved surface of the wire guidance portion,
such that the wire delivery device can be located in an access tunnel and wire passed through the bore from the proximal end to the exit hole, and can then be guided over the first curved surface of the wire guidance portion into the cavity at the distal end of the implant.

Preferably the wire delivery device is also provided in combination with an inner guide tube. Thus there may be a wire delivery kit that comprises the wire delivery device and the inner guide tube.

The inner guide tube comprises:
an elongate body having a proximal end and a distal end, wherein a flexible section of the elongate body is provided that extends from the distal end to a junction point, the flexible section being formed from a material that is sufficiently flexible that the flexible section can bend so that the elongate body can form a J-shape;
the elongate body having a bore running from its proximal end to its distal end,
such that the inner guide tube can be located in the bore of the wire delivery device, with the flexible section extending from the exit hole and over the first curved surface of the wire guidance portion.

The wire can then still be passed through the bore of the wire delivery device, from the proximal end to the exit hole, and can then be guided over the first curved surface of the wire guidance portion into the cavity at the distal end of the implant. However, when the inner guide tube is located in the wire delivery device, the wire can pass through the bore of the inner guide tube, from the proximal end to the distal end of the inner guide tube, and the shape of this inner guide tube eases the passage of the wire into the cavity.

The invention therefore provides a method of removing an implant, especially a femoral implant, from the surrounding tissue, the method comprising:
creating two access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant, wherein the anterior access tunnel is spaced from and substantially parallel to the anterior surface of the implant and the posterior access tunnel is spaced from and substantially parallel to the posterior surface of the implant;
removing bony ingrowth located adjacent to the anterior access tunnel, and removing bony ingrowth located adjacent to the posterior access tunnel and the posterior surface of the implant, to extend the width of the access tunnels;
removing bony ingrowth located at the distal end of the implant, to create a cavity at the distal end of the implant that extends in the medial and lateral directions;
removing bony ingrowth located at the antro-lateral edge of the implant, at the antro-medial edge of the implant, at the postro-lateral edge of the implant and at the postro-medial edge of the implant;
providing a wire to extend from a first access point at the proximal surface of the surrounding tissue to a second access point at the proximal surface of the surrounding tissue, via the anterior access tunnel, the cavity at the distal end of the implant and the posterior access tunnel, the wire comprising a cutting portion;
using the cutting portion of the wire to cut away bony ingrowth at a first surface of the implant;
providing a wire to extend from a first access point at the proximal surface of the surrounding tissue to a second access point at the proximal surface of the surrounding tissue, via the anterior access tunnel, the cavity at the distal end of the implant and the posterior access tunnel, the wire comprising a cutting portion; and using the cutting portion of the wire to cut away bony ingrowth at a second surface of the implant, wherein the first surface of the implant is either the medial or lateral surface of the implant, and the second surface of the implant is either the medial or lateral surface of the implant, and the first surface and the second surface are not the same.

Alternatively, in an alternate fifth stage, the procedure involves removing bony ingrowth located at the antro-lateral edge of the implant, at the antro-medial edge of the implant, at the postro-lateral edge of the implant and at the postro-medial edge of the implant. The intention of this step is to remove bony ingrowth from sections of both the medial and lateral aspects of the implant.

Therefore the medial surface of the implant is cleared of bony ingrowth at or near to where it adjoins the anterior surface of the implant and at or near to where it adjoins the posterior surface of the implant. The lateral surface of the implant is cleared of bony ingrowth at or near to where it adjoins the anterior surface of the implant and at or near to where it adjoins the posterior surface of the implant.

This alternate fifth step of the procedure is suitably effected using a medial-lateral clearance device.

The medial-lateral clearance device may be a novel medial-lateral clearance device according to the invention.

The medial-lateral clearance device of the invention comprises:
  an elongate body having a proximal end that is provided with a handle and having a distal end that is blunt, the elongate body being in the shape of a flat plate that extends from a first elongate edge to a second elongate edge;
  a cutting portion extending outwardly from the elongate body and located at or near the distal end, the cutting portion being in the shape of a flat plate that extends from an inner elongate edge, which connects with the first elongate edge of the elongate body at a substantially 90 degree angle, wherein the flat plate is further defined by a blunt edge that is located towards the distal end of the elongate body and a cutting edge that is located towards the proximal end of the elongate body;
such that the medial-lateral clearance device can be located in an access tunnel, with its flat plate elongate body in said tunnel and the flat plate cutting portion located alongside and substantially parallel to the surface of the implant, and can be moved towards the distal end of the implant until the flat plate cutting portion is completely located in a cavity at the distal end of the implant that extends in the medial and lateral directions, and the device can then be rotated by ninety degrees, such that the flat plate elongate body is located alongside and substantially parallel to the surface of the implant, with the flat plate cutting portion extending beneath the implant, and the flat plate elongate body can then be moved in a direction parallel to the surface of the implant until the flat plate cutting portion is aligned with either the medial or lateral surface of the implant, such that the medial-lateral clearance device can then be withdrawn posteriorly, with the flat plate elongate body alongside the anterior or posterior surface and the flat plate cutting portion alongside the medial or lateral surface, such that as the device is withdrawn the cutting edge of the device cuts away bony ingrowth located at said medial or lateral surface of the implant.

The skilled reader will appreciate that there is a "left handed" version of this device and a "right handed" version of this device. The difference is whether the flat plate cutting portion is ninety degrees clockwise from the flat plate elongate body or ninety degrees anticlockwise from the flat plate elongate body. To clear the medial surface of bony ingrowth at or near to where it adjoins the anterior surface of the implant and at or near to where it adjoins the posterior surface of the implant both versions of the device will be required. Equally, to clear the lateral surface of the implant of bony ingrowth at or near to where it adjoins the anterior surface of the implant and at or near to where it adjoins the posterior surface of the implant will require both versions of the device.

Therefore it is preferred that a medial-lateral clearance kit is provided that comprises a medial-lateral clearance device where the flat plate cutting portion is ninety degrees clockwise from the flat plate elongate body and a medial-lateral clearance device where the flat plate cutting portion is ninety degrees anticlockwise from the flat plate elongate body.

A first medial-lateral clearance device is used in the anterior access tunnel, so as to clear the medial surface of the implant of bony ingrowth at or near to where it adjoins the anterior surface of the implant. That medial-lateral clearance device is also used in the posterior access tunnel, so as to clear the lateral surface of the implant of bony ingrowth at or near to where it adjoins the posterior surface of the implant. A medial-second lateral clearance device is used in the anterior access tunnel so as to clear the lateral surface of the implant of bony ingrowth at or near to where it adjoins the anterior surface of the implant. That medial-lateral clearance device is also used in the posterior access tunnel, so as to clear the medial surface of the implant of bony ingrowth at or near to where it adjoins the posterior surface of the implant.

It is preferred that more than one size of medial-lateral clearance device is used in this stage. In particular, for both the "left handed" and "right handed" versions, a plurality of medial-lateral clearance devices may be provided, with each having a different width of cutting edge. Therefore the smallest size of cutting edge can be used first, e.g. that may be 1 mm to 4 mm wide, such as 3 mm. Then a larger size of cutting edge may be used, e.g. that may be 4 mm to 7 mm wide, such as 5 mm or 6 mm. There may be two different sizes, or three different sizes, or more.

The skilled reader will understand that the medial surface of the implant is cleared from both the anterior and posterior directions, and thus a cutting edge of 5 mm on both the left and right handed versions of the device would lead to a clearance of 10 mm in total on the medial surface. Likewise, the lateral surface of the implant is cleared from both the anterior and posterior directions, and thus a cutting edge of 5 mm on both the left and right handed versions of the device would lead to a clearance of 10 mm in total on the lateral surface.

It may be preferred to have a largest size of cutting edge that is equal to half the width of the medial surface/lateral surface, or that is greater than half the width of the medial surface/lateral surface. If it is exactly half, this will mean that there is clearance of bony ingrowth across the full width of that surface. If it is greater than half, then the middle part of that surface will have bony ingrowth cleared from both the anterior and posterior directions.

However, in other embodiments, the largest size of cutting edge may be less than half the width of the medial surface/lateral surface. This may, for example, be the case for large femoral implants. In that case, there will be a strip of bony ingrowth that remains, towards the centre of the medial surface and towards the centre of the lateral surface. However, this may, for example, be de-bonded with a firm tap using a metal hammer on the taper of the implant in both a posterior and anterior direction.

The present invention provides each of the above mentioned items as apparatus/devices individually.

The present invention also provides a kit comprising any two or more such devices, such as any three or more, any four or more such devices. In one embodiment there is a kit comprising all of the above mentioned apparatus/devices.

The present invention also provides a method in which all of the above steps are carried out. Preferably one or more of the above mentioned items are used in the method as apparatus/devices, e.g. the method may use any two or more such devices, such as any three or more, or any four or more such devices. In one embodiment the method comprises use of all of the above mentioned types of apparatus/devices.

DETAILED DESCRIPTION OF THE INVENTION

First Step

The first step of the surgical procedure is suitably effected using a targeting kit, which ensures the access tunnels are created at the required locations on the anterior and posterior of the implant. The access tunnels may be created using conventional tools, such as a drill and drill bits.

The targeting kit of the invention comprises:
a mounting arrangement for releasably mounting the targeting kit on the head or neck of a femoral implant,
first and second guide members, each of which is an elongate shape with a bore running along its longitudinal axis, each guide member being able to receive a drill bit through its bore,
a holding arrangement for holding the first and second guide members, the holding arrangement being adjustable between a release condition, in which the positions of the first and second guide members are adjustable relative to each other, and a holding condition, in which the first and second guide members are held by the holding arrangement in a fixed position relative to each other,
a bridging arrangement between the mounting arrangement and the first and second guide members, to space the first and second guide members from the mounting arrangement, with the bridging arrangement being adjustable between a release condition, in which the position of the mounting arrangement is adjustable relative to the first and second guide members, and a holding condition, in which the first and second guide members are fixedly spaced from the mounting arrangement by the bridging arrangement, such that the mounting arrangement can be secured onto the head or neck of the implant, with the first and second guide members being located on the base of the neck or the shoulder of the implant (preferably the shoulder of the implant), with the first guide member located at the anterior of the implant and the second guide member located at the posterior of the implant, the first guide member being angled such that its longitudinal axis is spaced from and substantially parallel to the anterior surface of the implant and the second guide member being angled such that its longitudinal axis is spaced from and substantially parallel to the posterior surface of the implant.

The guide members are placed on the midpoint of the medial-lateral axis of the shoulder of the implant, and pointing towards the midpoint of the medial-lateral axis of the implant.

Targeting Kit—First Design

The mounting arrangement for releasably mounting the targeting kit on the head or neck of a femoral implant suitably comprises a clamping component. This may be a clamping component that includes an elongate bore within which the neck of the femoral implant can be received. Thus the clamping component is suitably sized and shaped to be able to fit round and engage with part of the neck of a femoral implant.

For example, the clamping component may be a jig with a central elongate bore. The bore may have an adjustable sized diameter. It will be appreciated that in this embodiment the diameter of the bore of the clamping component may be adjusted to correspond to the outer diameter of the neck of the femoral implant that is being used. It may be that the jig can be adjusted between a position where the bore can be accessed and can receive a neck of a femoral implant, and a position where the jig is clamped shut and therefore any neck located within the bore is secured therein.

Thus the clamping component may have an open configuration, in which it can be placed around the neck of the femoral implant, and a closed configuration, in which is can be clamped shut, with the bore of the clamping component securely receiving and holding the neck of the femoral implant. The clamping component may be locked in this closed configuration during use of the apparatus.

The first and second guide members may have a bore diameter sized to substantially correspond to the diameter of access tunnels that will be created. Thus a drill bit can be passed through the bore and can be used to drill an access tunnel of the desired diameter.

The guide members may be slidably adjustable relative to each other, such that the distance between the guide members can be increased or decreased as required.

The distance between the guide members is suitably a value from 10 mm to 30 mm, e.g. from 15 to 25 mm.

Each guide member may be secured to the holding arrangement in any suitable fashion. In one embodiment the guide members are secured to the holding arrangement by the use of securing bores in the holding arrangement that are shaped and sized to receive the guide members.

The distance between the guide members can therefore be adjusted by adjusting the distance between the securing bores.

The skilled reader will appreciate that there are various options available for providing two securing bores in a manner such that the distance between them can be adjusted and then fixing the securing bores at a desired distance apart.

The holding arrangement may comprise a body portion that can be located on the shoulder of the implant. The first of the securing bores is located at a distal end of the body portion and can be located against the anterior surface of the implant when the body portion is located on the shoulder of the implant. The second of the securing bores is located at a proximal end of the body portion and can be located against the posterior surface of the implant when the body portion is located on the shoulder of the implant. The distance between the bores can be adjusted, set and locked.

In one such embodiment the body portion has two parts. The first part includes the first of the securing bores and the second part includes the second of the securing bores. The first part and second part of the body portion can be connected together to form the body portion. The first part and second part may be connected together to provide a desired separation between the securing bores.

The body portion may comprise an adjustment member that allows the distance between the two parts to be altered.

In one embodiment each body part has an interlocking section extending therefrom, wherein each interlocking section has an elongate aperture, such that the two body parts can be fixed at a desired distance to each other by using a fastening member, such as a bolt, to extend through both elongate apertures and fix them together.

In another embodiment one body part has an interlocking section extending therefrom, with this interlocking section having an elongate aperture, and the other body part has an interlocking section extending therefrom, with this interlocking section having a fastening member that can extend through the elongate aperture and be secured thereto.

By selecting the position within the elongate aperture(s) where the fastening member is located, different separation distances can be achieved.

The bridging arrangement between the mounting arrangement and the first and second guide members serves to space the first and second guide members from the mounting arrangement. This can therefore reflect the distance between the neck of the femoral implant and the shoulder of the implant body.

The bridging arrangement is adjustable between a release condition, in which the position of the mounting arrangement is adjustable relative to the first and second guide members, and a holding condition, in which the first and second guide members are fixedly spaced from the mounting arrangement by the bridging arrangement.

The bridging arrangement can preferably allow the angle of the first and second guide members with respect to the mounting arrangement to be adjusted. This can therefore reflect the fact that the angle of the posterior surface towards the distal end of the implant, and the angle of the anterior surface towards the distal end of the implant, are not the same as the angle at which the femoral neck is positioned on the shoulder of the implant body. This allows for the fact that the femoral implants used in surgery have different angles between the head/neck and the shoulder portions.

The bridging arrangement may suitably permit the mounting arrangement and the first and second guide members to be pivotably adjustable relative to each other, such that the angle between the mounting arrangement and the first and second guide members can be increased or decreased as required.

The angle between the mounting arrangement and the first and second guide members is suitably a value from 0 degrees to 90 degrees, e.g. from 10 to 80 degrees or from 15 to 75 degrees. In one embodiment the angle can be adjusted between an angle of from 5 degrees to 60 degrees, such as from 10 to 55 degrees.

Therefore the bridging arrangement permits the mounting arrangement and the first and second guide members to be pivotably adjustable relative to each other, such that the angle between the mounting arrangement and the first and second guide members can be increased or decreased as required.

The head-neck angle on an implant is usually in the range of from 120 to 150 degrees, such as from 126 to 140 degrees. Therefore the angle between the mounting arrangement and the first and second guide members is suitably adjustable to be a value from 30 to 60 degrees, such as from 40 to 54 degrees.

In one embodiment the bridging arrangement includes a ratchet and pinion system to permit the mounting arrangement and the first and second guide members to be pivotably adjustable relative to each other. It may be that the mounting arrangement is attached to a first mounting base, and the first mounting base is connected to the ratchet and pinion system.

It may be that the first and second guide members are attached to a second mounting base, and the second mounting base is connected to the ratchet and pinion system.

In one embodiment, the first mounting base pivotably moves with respect to the second mounting base via the ratchet and pinion system, thereby altering the angle between the mounting arrangement and the first and second guide members. In this regard, the second mounting base may be fixedly connected to the ratchet and pinion system, directly or indirectly, whilst the first mounting base is moveably connected to the ratchet and pinion system, directly or indirectly.

In an alternative embodiment, the second mounting base pivotably moves with respect to the first mounting base via the ratchet and pinion system, thereby altering the angle between the mounting arrangement and the first and second guide members. In this regard, the first mounting base may be fixedly connected to the ratchet and pinion system, directly or indirectly, whilst the second mounting base is moveably connected to the ratchet and pinion system, directly or indirectly.

The pivoting movement of the mounting arrangement and the first and second guide members with respect to each other is about a pivot point. This pivot point may be a ball joint, e.g. a restricted articulation ball joint.

In one embodiment, the first mounting base connects the bridging arrangement to the mounting arrangement.

In one embodiment, the first mounting base connects the bridging arrangement to the holding arrangement.

In one embodiment, the first mounting base connects the bridging arrangement to both the mounting arrangement and the holding arrangement.

It may be that the first mounting base connects with the holding arrangement at or near the pivot point about which the relative pivotal movement of the mounting arrangement and the first and second guide members occurs.

The pivoting movement via the ratchet and pinion system may suitably be effected by the user via a thumb wheel or other manual controller.

The bridging arrangement suitably includes a locking mechanism for locking the mounting arrangement relative to the first and second guide members once they are at the desired angle to each other.

Extra Medullary Targeting Device to be Used with First Design

Preferably the above design of kit is used in combination with an extra medullary targeting device. The extra medullary targeting device comprises:
 a targeting kit interlocking portion,
 an extra medullary guidance portion, and
 a holding arrangement for holding and spacing the targeting kit interlocking portion and the extra medullary guidance portion,
wherein the targeting kit interlocking portion comprises:
 a first guide member interlocking component, which comprises a bore within which the first guide member of the targeting kit can be received, and
 a second guide member interlocking component, which comprises a locking pin that can be received in the bore of the second guide member of the targeting kit, wherein the elongate axis of the locking pin is parallel to the longitudinal axis of the bore,
wherein the extra medullary guidance portion comprises a bore within which a test pin having an elongate body can be received, wherein the length of the pin's elongate body is greater than the length of the bore, such that when the test pin is received within the bore, a portion of its elongate body extends out from the exit end of the bore, and wherein the holding arrangement holds the two portions fixedly relative to each other in terms of their angle, such that the bore of the first guide member interlocking component and the bore of the extra medullary guidance portion have their longitudinal axes aligned, such that these bores run parallel to each other, but with the holding arrangement being adjustable in terms of the distance between the two portions, with this holding arrangement being adjustable between a release condition, in which the distance between the two portions is adjustable, and a holding condition, in which the distance between the two portions is fixed, such that the bore of the first guide member interlocking component can receive the first guide member of the targeting kit, and the locking pin of the second guide member interlocking component can be received in the bore of the second guide member of the targeting kit and such that the test pin can be received within the bore of the extra medullary guidance portion, such that the bore of the first guide member interlocking component is angularly aligned with the first guide member of the targeting kit, and such that the locking pin of the second guide member interlocking component is angularly aligned with the second guide member of the targeting kit and such that the test pin located in the bore of the extra medullary guidance portion is consequently also angularly aligned with the first and second guide members of the targeting kit, such that the alignment of the test pin can be checked, to ensure that it is pointing to the distal tip of implant, as determined via x-ray, or the middle of the medio-lateral diameter of the femur at the level of the distal tip of the implant.

The targeting kit interlocking portion and the extra medullary guidance portion may be slidably adjustable relative to each other, such that the distance between the portions can be increased or decreased as required.

The distance between the portions is suitably a value from 20 mm to 70 mm, e.g. from 30 to 60 mm; for example the distance may be adjustable from a minimum of 34 mm and a maximum of 52 mm.

Each portion may be secured to the holding arrangement in any suitable fashion.

The skilled reader will appreciate that there are various options available for providing two portions in a manner such that the distance between them can be adjusted and then fixing the portions at a desired distance apart.

The holding arrangement may comprise a body section. The targeting kit interlocking portion is located towards a distal end of the body section and the extra medullary guidance portion is located towards a proximal end of the body section. The distance between the portions can be adjusted, set and locked.

In one such embodiment the body section has two parts. The first part includes the targeting kit interlocking portion and the second part includes the extra medullary guidance portion. The first part and second part of the body section can be connected together to form the body section. The first part and second part may be connected together to provide a desired separation between the targeting kit interlocking portion and the extra medullary guidance portion.

The body section may comprise an adjustment member that allows the distance between the two parts to be altered.

In one embodiment each body part has an interlocking section extending therefrom, wherein each interlocking section has an elongate aperture, such that the two body parts can be fixed at a desired distance to each other by using a fastening member, such as a bolt, to extend through both elongate apertures and fix them together.

In another embodiment one body part has an interlocking section extending therefrom, with this interlocking section having an elongate aperture, and the other body part has an interlocking section extending therefrom, with this interlocking section having a fastening member that can extend through the elongate aperture and be secured thereto.

By selecting the position within the elongate aperture(s) where the fastening member is located, different separation distances can be achieved.

The locking pin may have any suitable length of elongate body. In one embodiment, its length is a value from 20 mm to 120 mm, e.g. from 30 to 100 mm; for example it may be a length between 40 and 80 mm.

The test pin may have any suitable length of elongate body. In one embodiment, its length is a value from 50 mm to 300 mm, e.g. from 70 to 250 mm; for example it may be a length between 100 and 200 mm.

The distance between the first guide member interlocking component, and the second guide member interlocking component clearly should be such that it corresponds with the distance between the first and second guide members of the targeting kit, so that the bore of the first guide member interlocking component can receive the first guide member of the targeting kit at the same time as the locking pin of the second guide member interlocking component is received in the bore of the second guide member of the targeting kit.

Second Design

An alternative design is as follows:

The mounting arrangement for releasably mounting the targeting kit on the head of a femoral implant suitably comprises a cup-shaped component. This cup-shaped component is sized and shaped to be able to fit round and engage with part of the head of a femoral implant.

It may be that the cup-shaped component has a fixed size of inner diameter that corresponds to the outer diameter of the head of the femoral implant that is being used. It will be appreciated that in this embodiment a number of different cup-shaped components may be provided, each having a different inner diameter, and the one having the required inner diameter can be selected based on the size of the head of the femoral implant that is being used.

In another embodiment, the cup-shaped component has an adjustable size of inner diameter. For example, the cup-shaped component may be made up of a number of nested layers and by removing one or more layers the inner diameter will be increased whilst by adding one or more inner layers the inner diameter will be decreased. It will be appreciated that in this embodiment the inner diameter of the cup-shaped component may be adjusted to correspond to the outer diameter of the head of the femoral implant that is being used.

The first and second guide members may have a bore diameter sized to substantially correspond to the diameter of access tunnels that will be created. Thus a drill bit can be passed through the bore and can be used to drill an access tunnel of the desired diameter.

The guide members may be slidably adjustable relative to each other, such that the distance between the guide members can be increased or decreased as required.

The distance between the guide members is suitably a value from 10 mm to 30 mm, e.g. from 15 to 25 mm.

The guide members may optionally be pivotably adjustable relative to each other, such that the angle between the guide members can be increased or decreased as required. This allows for the fact that the femoral implants used in surgery have different degrees of taper on their bodies.

The angle between the guide members is suitably a value of 10 degrees or less, such as from 1 to 5 degrees, e.g. from 2 to 4 degrees.

Each guide member may be secured to the holding arrangement in any suitable fashion. In one embodiment the guide members are secured to the holding arrangement by the use of securing bores in the holding arrangement that are shaped and sized to receive the guide members.

The distance between the guide members can therefore be adjusted by adjusting the distance between the securing bores.

The angle between the guide members can therefore be adjusted by adjusting the angle between the securing bores.

The skilled reader will appreciate that there are various options available for providing two securing bores in a manner such that the distance between them can be adjusted and then fixing the securing bores at a desired distance apart.

Equally, the skilled reader will appreciate that there are various options available for providing two securing bores in a manner such that the angle between them can be adjusted and then fixing the securing bores at a desired angle to one another.

The holding arrangement may comprise two body portions, each of which can be secured to one of the guide members, and an adjustment member that allows the distance and/or angle between the two body portions to be altered.

In one embodiment each body portion has an interlocking section extending therefrom, wherein each interlocking section has an elongate aperture, such that the two body portions can be fixed at a desired distance and angle to each other by using a fastening member, such as a bolt, to extend through both elongate apertures and fix them together.

In another embodiment one body portion has an interlocking section extending therefrom, with this interlocking section having an elongate aperture, and the other body portion has an interlocking section extending therefrom, with this interlocking section having a fastening member that can extend through the elongate aperture and be secured thereto.

By selecting the position within the elongate aperture(s) where the fastening member is located, different separation distances and angles can be achieved.

The provision of the elongate apertures therefore allows the relative positions of the two body portions, both in terms of their distance apart and angle to one another, to be adjusted as required.

The bridging arrangement between the mounting arrangement and the first and second guide members serves to space the first and second guide members from the mounting arrangement, to reflect the fact that there is a distance between the head of a femoral implant and the shoulder of the implant body. The bridging arrangement is adjustable between a release condition, in which the position of the mounting arrangement is adjustable relative to the first and second guide members, and a holding condition, in which the first and second guide members are fixedly spaced from the mounting arrangement by the bridging arrangement.

The bridging arrangement may permit the mounting arrangement and the first and second guide members to be slidably adjustable relative to each other, such that the distance between the mounting arrangement and the first and second guide members can be increased or decreased as required.

The distance between the mounting arrangement and the first and second guide members is suitably a value from 10 mm to 30 mm, e.g. from 15 to 25 mm.

The bridging arrangement may optionally permit the mounting arrangement and the first and second guide members to be pivotably adjustable relative to each other, such that the angle between the mounting arrangement and the first and second guide members can be increased or decreased as required. This allows for the fact that the femoral implants used in surgery have different angles between the head and the shoulder portions.

The head-neck angle on an implant is usually in the range of from 120 to 150 degrees, such as from 126 to 140 degrees. Therefore the angle between the mounting arrangement and the first and second guide members is suitably a value from 30 to 60 degrees, such as from 40 to 54 degrees.

It may be that the bridging arrangement includes an elongate aperture and a fastening member that can extend through the elongate aperture and be secured thereto.

In one embodiment the elongate aperture is linked to the first and second guide members (e.g. via the holding arrangement) and the fastening member is linked to the mounting arrangement.

In one embodiment the elongate aperture is linked to the mounting arrangement and the fastening member is linked to the first and second guide members (e.g. via the holding arrangement).

The fastening member can extend through the elongate aperture and can then be secured in position, fixing the elongate aperture and the fastening member together.

In these embodiments, therefore the bridging arrangement includes one elongate aperture and a fastening member that can extend through the elongate aperture and be secured thereto.

However, alternative embodiments can also be envisaged where the bridging arrangement includes two elongate apertures and a fastening member that can extend through both the elongate apertures and be secured thereto.

Thus there may be a first elongate aperture linked to the mounting arrangement and a second elongate aperture linked to the first and second guide members (e.g. via the holding arrangement) and then the fastening member, such as a bolt, can extend through both elongate apertures and fix them together.

By selecting the position within the elongate aperture(s) where the fastening member is located, different separation distances and angles can be achieved.

Thus the provision of the one or two elongate apertures allows the relative positions of the first and second guide members and the mounting arrangement, both in terms of their distance apart and angle to one another, to be adjusted as required.

The targeting kit of the invention is beneficial due to the fact that it is secured on the head or neck of the implant, as compared to prior devices which have been designed to be secured on the tapered body of the implant and which therefore have a predetermined angle of inclination for the guide members. The targeting kit of the invention is able to have the angle of the guide members adjusted to reflect the variety of taper angles found on femoral implants. It can therefore be readily used on a range of implants.

Second Step

The second stage of the procedure involves removing bony ingrowth located adjacent to the anterior access tunnel, and removing bony ingrowth located adjacent to the posterior access tunnel and the posterior surface of the implant. The intention of this step is to extend the width of the access tunnels, preferably so that their widths substantially correspond with the width of the implant. Therefore the anterior access tunnel is broadened in a plane that is substantially parallel to the anterior surface of the implant, and the posterior access tunnel is broadened in a plane that is substantially parallel to the posterior surface of the implant. This may be carried out using the osteotome device of the invention (or a set of two or more osteotome devices according to the invention).

The osteotome device of the invention comprises:
- an elongate body having a proximal end that is provided with a handle and a distal end that is blunt, wherein the elongate body includes a distal section extending from the distal end to a shoulder point, and an indented section extending from the shoulder point towards the proximal end, wherein the depth of the distal section is greater than the depth of the indented section and wherein the shoulder point is located closer to the distal end than the proximal end;
- a cutting portion extending from the indented section of the elongate body, the cutting portion having a front face and a back face, the back face being attached to the indented section of the elongate body, wherein the distance between the back face and the front face is substantially the same as the difference in depth between the distal section and the indented section of the elongate body, and wherein the front face of the cutting portion is blunt but is connected to the back face by a first cutting side and a second cutting side, the first cutting side and the second cutting side each being at least partially located outwardly of the elongate body;
- such that the osteotome device can be located in an access tunnel and pushed towards the distal end of the implant so as to cut away bony ingrowth with the first cutting side and the second cutting side.

The elongate body suitably has a diameter that is equal to or slightly less than the diameter of the access tunnel. For example its diameter may be less than the diameter of the access tunnel by 1 mm or less, e.g. from 0.1 to 0.5 mm.

In one embodiment the shoulder point is located at a distance from the distal end of from 0.5 to 20 mm, such as from 0.5 to 15 mm or from 0.5 to 10 mm; preferably it is at a distance from the distal end of from 1 to 8 mm, such as from 1.5 to 7 mm or from 2 to 6 mm, e.g. from 2.5 to 5 mm.

Preferably the cutting portion has a front face that is substantially planar.

Preferably the cutting portion is triangular in cross sectional shape, with two of the three sides of the triangle being the first cutting side and the second cutting side. Preferably the third side of the triangle is blunt but this is not essential.

The use of a triangular shape means that at least part of the first cutting side and at least part of the second cutting side can angularly extend outwardly of the elongate body, providing cutting surfaces for cutting away bony ingrowth.

In one embodiment the triangle is isosceles, i.e. there are two sides the same length. In one embodiment the triangle is equilateral i.e. all three sides are the same length. However, the triangle may also be scalene, i.e. the sides are all different lengths.

It can be that the first cutting side and the second cutting side are the same length (or at least substantially the same length, within manufacturing tolerances). This has the benefit of providing cutting at the same angle regardless of whether the first cutting side or the second cutting side is used to cut.

In one embodiment first cutting side and the second cutting side are at an angle to one another of from 55 to 75 degrees, such as from 60 to 70 degrees, e.g. from 62 to 68 degrees, for example about 65 degrees.

By providing the cutting portion in the indented section of the elongate body, with the distance between the back face and the front face being substantially the same as the difference in depth between the distal section and the indented section of the elongate body, the front face of the cutting portion does not protrude outwardly from the elongate body.

However, at least part of the first cutting side and at least part of the second cutting side do extend outwardly from the elongate body, allowing them to cut away bony ingrowth.

In one embodiment the cutting portion is replaceably secured to the elongate body, therefore allowing the cutting portion to be removed and replaced when the cutting sides are not sharp enough for continued use.

In another embodiment the cutting portion is not replaceable and therefore the osteotome device is simply disposed of once the cutting sides are not sharp enough for continued use.

Where a set of two or more osteotome devices according to the invention is used, these may differ in terms of the width of cutting portion (distance between the first cutting side and a second cutting side). Therefore within the set each osteotome device may be provided with a width of cutting portion that is slightly wider than the one that is the size below, e.g. the width may be 0.5 mm wider or more, or 1mm wider or more, such as from 1 mm to 5 mm wider.

Third Step

The third stage of the procedure involves removing bony ingrowth located between the implant and the femur in the anterior aspect, and removing bony ingrowth located between the implant and the femur in the posterior aspect. The intention of this step is to reduce the amount of bony ingrowth between the implant and the femur in the anterior aspect and to reduce the amount of bony ingrowth between the implant and the femur in the posterior aspect. This may be carried using the curette device of the invention (or a set of two or more curette devices according to the invention).

The curette device of the invention comprises:
- an elongate body having a proximal end that is provided with a handle and having a distal end that is blunt;
- a cutting portion extending outwardly from the elongate body and located at or near the distal end, the cutting portion having a blunt edge and a cutting edge, wherein the cutting edge is at an angle of from 30 to 150 degrees to the elongate axis of the elongate body and wherein the blunt edge is substantially parallel to the elongate axis of the elongate body;
- such that the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

The elongate body of the curette device suitably has a diameter that is equal to or slightly less than the diameter of the access tunnel. For example its diameter may be less than the diameter of the access tunnel by 1 mm or less, e.g. from 0.1 to 0.5 mm.

The elongate body of the curette device is suitably in the form of a flat plate. Thus it may extend from a first elongate edge to a second elongate edge. In one embodiment, its width is from 2 to 7 mm, such as from 3 to 6 mm, e.g. about 4 to 5 mm.

As the elongate body is in the form of a plate, its depth (thickness) will be less than its width. In one embodiment its depth is less than or equal to half of its width. In one embodiment the depth of the plate is from 0.2 to 2 mm, such as from 0.5 to 1.5 mm, preferably from 1 to 1.5 mm.

The length of the elongate body is suitably greater than the length of the implant. For example its length may be greater than the length of the implant by 1 mm or more, such as 3 mm or more, or 5 mm or more.

The cutting portion will have an attachment edge which is the edge by which the cutting portion is attached to the elongate body. This attachment edge may be attached to the second elongate edge of the body of the curette device when said body is in the form of a flat plate. The cutting portion additionally has the cutting edge and the blunt edge. Optionally there may be further edges.

In one embodiment the cutting portion is substantially plate-like in shape. Thus it may have two substantially flat faces that are defined by the above-mentioned edges.

The cutting edge is located towards the proximal end of the cutting portion, i.e. such that cutting occurs as the curette device is withdrawn from the tunnel rather than as it is pushed into the tunnel.

The cutting edge may be sharp along its length, such that all of the cutting edge can serve to cut away bony ingrowth located between the access tunnel and the surface of the implant. However, it will be appreciated that the device will also be effective if only some of the length of the cutting edge is sharp. In the present invention, it is only necessary that the cutting edge is sharp at its distal end, i.e. the end furthest from the attachment edge. Therefore the cutting edge is sharp at its distal end and is optionally sharp along some or all of the remainder of the cutting edge.

In some embodiments the cutting edge is sharp at said distal end and also is sharp for 10% or more of the remainder of the cutting edge, e.g. 20% or more, 30% or more, 40% or more, or 50% or more. In some embodiments the cutting edge is sharp at said distal end and is also sharp for 10% or less of the remainder of the cutting edge, e.g. 5% or less. Where portions of the cutting edge apart from the distal end are sharp, preferably these are located near to the distal end.

For example, going from the distal end towards the proximal end of the cutting edge, the first 10% or more of the length may be sharp, e.g. the first 15% or more, the first 25% or more, or the first the first 35% or more, or the first 50% or more.

The cutting edge suitably adjoins the elongate body near to the distal end of the elongate body. In one embodiment the point at which the cutting edge adjoins the elongate body is located at a distance from the distal end of from 0.5 to 20 mm, such as from 0.5 to 15 mm or from 0.5 to 10 mm; preferably it is at a distance from the distal end of from 1 to 8 mm, such as from 1.5 to 7 mm or from 2 to 6 mm, e.g. from 2.5 to 5 mm.

The cutting edge may be angled upwardly, i.e. an angle of from 30 to 89 degrees to the elongate axis of the elongate body, or may be angled downwardly, i.e. an angle of from 91 to 150 degrees to the elongate axis of the elongate body. It may also be at an angle of about 90 degree. Either permits the user of the device to angle the device whilst it is in the access tunnel so as to result in the cutting edge contacting the bony ingrowth at the edge of the tunnel, and thus permitting the bony ingrowth between the face of the implant and the femoral cortex to be scraped away.

Preferably the cutting edge is at an angle of from 30 to 60 degrees to the elongate axis of the elongate body or is at an angle of from 120 to 150 degrees to the elongate axis of the elongate body.

In one embodiment the distance from the elongate body (e.g. from its second elongate edge) to the distal end of the cutting edge, when measured in a direction that is perpendicular to the elongate axis of the elongate body, is from 3 to 10 mm, such as from 4 to 9 mm, e.g. from 5 to 8 mm.

The cutting edge may be straight or may be curved. If it is curved, its angle to the elongate axis should be seen as the angle created when considering the notional straight line between the distal end and the proximal end of the cutting edge with respect to the elongate axis.

The blunt edge may be straight or may be curved. If it is curved, its angle to the elongate axis should be seen as the angle created when considering the notional straight line between the distal end and the proximal end of the blunt edge with respect to the elongate axis.

In one embodiment the cutting portion is replaceably secured to the elongate body, therefore allowing the cutting portion to be removed and replaced when the cutting edge is not sharp enough for continued use.

In another embodiment the cutting portion is not replaceable and therefore the curette device is simply disposed of once the cutting edge is not sharp enough for continued use.

Where a set of two or more curette devices according to the invention is used, these may differ in terms of the length of the cutting edge (distance between the distal end and the proximal end of the cutting edge) and/or in terms of the distance from the elongate body (e.g. from its second elongate edge) to the distal end of the cutting edge, when measured in a direction that is perpendicular to the elongate axis of the elongate body. Therefore within the set each curette device may be provided with such a length/distance that is slightly greater than the one that is the size below, e.g. said length/distance may be 0.5 mm greater or more, or 1 mm greater or more, such as from 1 mm to 5 mm greater.

Fourth Step

The fourth stage of the procedure involves removing bony ingrowth located at the distal end of the implant, to create a cavity at the distal end of the implant that extends in the medial and lateral directions. This stage may be carried out using the medial-lateral cavity maker device of the invention (or a set of two or more medial-lateral cavity maker devices according to the invention).

The medial-lateral cavity maker device of the invention comprises:
  an elongate body having a proximal end that is provided with a handle and a distal end that is blunt;
  a cutting portion extending outwardly from the elongate body, the cutting portion being located closer to the distal end of the elongate body than the proximal end of the elongate body, the cutting portion having a connecting end attached to the elongate body and a protruding end located away from the elongate body, the connecting end and the protruding end being connected by a first edge located towards the distal end of the elongate body and a second edge located towards the proximal end of the elongate body, wherein the first edge is blunt but the second edge is a cutting edge;
  such that the medial-lateral cavity maker device can be located in an access tunnel and rotated so as to cut away bony ingrowth with the second edge at the distal end of the implant, to create a cavity at the distal end of the implant that extends in the medial and lateral directions.

The elongate body suitably has a diameter that is equal to or slightly less than the minimum diameter of the access tunnel. For example its diameter may be less than the minimum diameter of the access tunnel by 1 mm or less, e.g. from 0.1 to 0.5 mm.

The cutting portion suitably extends in a plane that lies on the edge of the elongate body. This allows the cutting portion to be positioned parallel to the surface of the implant when the cutting portion is in a part of the access tunnel that is alongside the implant, with the cutting portion only then being rotated once the cutting portion is located beyond the distal end of the implant. This reflects the fact that the access tunnel is only widened in the second step of the procedure in a direction parallel to the surface of the implant; the dimensions of the access tunnel in all other directions remain relatively small. Therefore the extending portion of the cavity maker device, namely the cutting portion, needs to be able to be positioned in that widened dimension of the access tunnel so that it can pass down to a location beyond the distal end of the implant.

In one embodiment the cutting portion is located at the distal end of the elongate body. In another embodiment the cutting portion is located at a distance from the distal end of from 0.5 to 20 mm, such as from 0.5 to 15 mm or from 0.5 to 10 mm; preferably it is at a distance from the distal end of from 1 to 8 mm, such as from 1.5 to 7 mm or from 2 to 6 mm, e.g. from 2.5 to 5 mm.

The cutting portion has an upper surface and a lower surface linking the first edge and the second edge. These surfaces may suitably be substantially flat. These surfaces are suitably blunt.

The cutting portion is such that in use the first edge is a curved edge that is convex and the second edge is a curved edge that is concave. The cutting portion may overall have a hook shape.

It may be that the cutting portion has a fixed shape that is curved. In particularly it may have a fixed hook shape that curves upwardly (that is, towards the proximal end rather than the distal end).

In another embodiment the cutting portion is only formed into a curved shape in situ. For example, the cutting portion may be formed from a plurality (e.g. three or more, such as from three to twenty, or from three to ten) of hinged sections that can flex in an upward direction (that is, towards the proximal end rather than the distal end) and which therefore can form a curved shape when they are located at the distal end of the implant. In one embodiment, the hinged sections may be linked by a tension wire which can be shortened in order to increase the tension and urge the hinged sections upwardly. The hinged sections may be universal joints.

In this embodiment preferably the cutting portion is formed from a plurality (e.g. three or more, such as from three to twenty, or from three to ten) of hinged sections that can only flex in an upward direction (that is, towards the proximal end rather than the distal end). Thus there is no movement in other directions.

In one embodiment the cutting portion is replaceably secured to the elongate body, therefore allowing the cutting portion to be removed and replaced when the cutting edge is not sharp enough for continued use.

In another embodiment the cutting portion is not replaceable and therefore the medial-lateral cavity maker device is simply disposed of once the cutting edge is not sharp enough for continued use.

When a set of two or more medial-lateral cavity maker devices according to the invention is used, these may differ in terms of the width of cutting portion (distance between the elongate body and the outermost point of the second edge of the cutting portion). Therefore within the set each medial-lateral cavity maker device may be provided with a width of cutting edge portion that is slightly wider than the one that is the size below, e.g. the width may be 0.5 mm wider or more, or 1 mm wider or more, such as from 1 mm to 5 mm wider.

Fifth Step

The fifth stage of the procedure involves providing a wire to extend from a first access point at the proximal surface of the surrounding tissue to a second access point at the proximal surface of the surrounding tissue via the anterior access tunnel, the cavity at the distal end of the implant and the posterior access tunnel. This stage may be carried out using the wire delivery device of the invention.

The wire may comprise a cutting portion that can be used to cut away bony ingrowth at the medial surface of the implant and the lateral surface of the implant.

Alternatively, the wire may be a lead wire that is initially located to extend from the first access point at the proximal surface of the surrounding tissue to the second access point at the proximal surface of the surrounding tissue via the anterior access tunnel the cavity at the distal end of the implant and the posterior access tunnel, and once this lead wire has been successfully located a cutting wire, which comprises a cutting portion that can be used to cut away bony ingrowth at the medial surface of the implant and the lateral surface of the implant, can be attached to one end of the lead wire and the lead wire can then be withdrawn by its other end, therefore feeding the cutting wire into its place. The cutting wire will therefore then extend from the first access point at the proximal surface of the surrounding tissue to the second access point at the proximal surface of the surrounding tissue via the anterior access tunnel the cavity at the distal end of the implant and the posterior access tunnel.

The cutting wire can then be used to cut away bony ingrowth at the medial surface of the implant.

The same process can then be repeated to provide cutting wire from the first access point at the proximal surface of the surrounding tissue to the second access point at the proximal surface of the surrounding tissue, and to use this wire to cut away bony ingrowth at the lateral surface of the implant.

Of course, it will be appreciated that the order of cutting could be reversed, such that bony ingrowth at the lateral side of the implant could be cut first, followed by the medial side.

For the sake of safety, a wire guide device of the type described in WO2011/045568 may be used for guiding the elongate cutting wire during the cutting of the bone. If a wire guide is used, this constrains movement of the cutting wire, thereby ensuring that the cutting takes through the material directly adjacent the implant.

During the cutting the surgeon may attach the ends of the wire to suitable handles, and can then manipulates the wire in a sawing action, retracting the length of the cutting wire up the bone and thereby cutting the bone away from the implant in respect of a first face of the implant. The surgeon repeats the process the second face of the implant. The first and second faces are the medial and lateral faces of the implant, and these may be dealt with in either order. Once the sawing action has been used to cut away the bone from both the medial and lateral faces of the implant this results in the implant being freed from the bone and therefore allows the implant to be removed.

The wire delivery device of the invention comprises:
an elongate body having a proximal end that is provided with a handle and a distal end that is blunt;
a wire guidance portion extending outwardly from the elongate body, the wire guidance portion being located closer to the distal end of the elongate body than the proximal end of the elongate body, the wire guidance portion having a connecting end attached to the elongate body and a protruding end located away from the elongate body, the connecting end and the protruding end being connected by a first curved surface and a second curved surface, the first curved surface being convex and being located towards the distal end of the elongate body and the second curved surface being concave and being located towards the proximal end of the elongate body;
the elongate body having a bore running from its proximal end to an exit hole located adjacent to or in the second curved surface of the wire guidance portion,
such that the wire delivery device can be located in an access tunnel and wire passed through the bore from the proximal end to the exit hole, and can then be guided into the cavity at the distal end of the implant.

In use the elongate body extends down the access tunnel and the wire guidance portion is located in the cavity beyond the distal end of the implant. The wire guidance portion will be moved to lie in a plane perpendicular to the anterior or posterior surface of the implant once the wire guidance portion is located beyond the distal end of the implant. Thus when a wire delivery device is provided in both the posterior and anterior access tunnels, and the wire guidance portion is moved to lie in a plane perpendicular to the anterior or posterior surface of the implant, a wire that is passed through the bore of the device, from the proximal end to the exit hole, and guided into the cavity from the anterior side will meet a wire that is passed through the bore of the device, from the proximal end to the exit hole, and guided into the cavity from the anterior side. Provided that the two wires are provided with suitable engagement means at their distal ends, e.g. hooks on each, or one with a hook and one with a loop, then the wires can be connected, forming a wire that runs down both access tunnels and round the cavity at the distal end of the implant.

The elongate body suitably has a diameter that is equal to or slightly less than the minimum diameter of the access tunnel. For example its diameter may be less than the minimum diameter of the access tunnel by 1 mm or less, e.g. from 0.1 to 0.5 mm.

The wire guidance portion suitably extends in a plane that lies on the edge of the elongate body. This allows the wire guidance portion to be positioned parallel to the surface of the implant when the wire guidance portion is in a part of the access tunnel that is alongside the implant, with the wire guidance portion only then being rotated (e.g. by 90 degrees) to lie in a plane perpendicular to the anterior or posterior surface of the implant, once the wire guidance portion is located beyond the distal end of the implant. This reflects the fact that the access tunnel is only widened in the second step of the procedure in a direction parallel to the surface of the implant; the dimensions of the access tunnel in all other directions remain relatively small. Therefore the extending portion of the wire guidance device, namely the wire guidance portion, needs to be able to be positioned in that widened dimension of the access tunnel so that it can pass down to a location beyond the distal end of the implant.

In one embodiment a device is used that is both a medial-lateral cavity maker device and a wire delivery device. It will be appreciated that a device may be provided that meets the requirements of both these devices of the invention.

Such a combined device would comprise:
an elongate body having a proximal end that is provided with a handle and a distal end that is blunt;
a wire guidance portion extending outwardly from the elongate body, this portion being a wire guidance portion and a cutting portion, the portion being located closer to the distal end of the elongate body than the proximal end of the elongate body, the portion having a connecting end attached to the elongate body and a protruding end located away from the elongate body, the connecting end and the protruding end being connected by a first curved surface and a second curved surface, the first curved surface being convex and being located towards the distal end of the elongate body and the second curved surface being concave and being located towards the proximal end of the elongate body and being a cutting surface;
the elongate body having a bore running from its proximal end to an exit hole located adjacent to or in the second curved surface of the wire guidance portion,
such that the combined device can be located in an access tunnel and rotated so as to cut away bony ingrowth with the cutting surface at the distal end of the implant, to create a cavity at the distal end of the implant that extends in the medial and lateral directions; and
such that the combined device can be located in an access tunnel and wire passed through the bore from the proximal end to the exit hole, and can then be guided into the cavity at the distal end of the implant.

However, in another embodiment the wire delivery device is not a medial-lateral cavity maker device. In such an embodiment the second curved surface may be blunt rather than a cutting surface.

The wire guidance portion has an upper face and a lower face linking the first curved surface and the second curved surface. These faces may suitably be substantially flat. These faces are suitably blunt.

The wire guidance portion may overall have a hook shape. Thus it may be provided in the form of a fixed hook shape that curves upwardly (that is, towards the proximal end rather than the distal end).

Preferably the exit hole is aligned with the second curved surface, so that a wire exiting the exit hole directly falls onto that concave surface. The exit hole may include a notch to assist with aligning a wire exiting the exit hole onto the centreline of the concave surface.

Preferably the wire delivery device is also provided in combination with an inner guide tube. Thus there may be a wire delivery kit that comprises the wire delivery device and the inner guide tube.

The inner guide tube comprises:
an elongate body having a proximal end and a distal end, wherein a flexible section of the elongate body is provided that extends from the distal end to a junction point, the flexible section being formed from a material that is sufficiently flexible that the flexible section can bend so that the elongate body can form a J-shape;
the elongate body having a bore running from its proximal end to its distal end,
such that the inner guide tube can be located in the bore of the wire delivery device, with the flexible section extending from the exit hole and over the first curved surface of the wire guidance portion.

A handle may be provided at the proximal end.

The wire can then still be passed through the bore of the wire delivery device, from the proximal end to the exit hole, and can then be guided over the first curved surface of the wire guidance portion into the cavity at the distal end of the implant. However, when the inner guide tube is located in the wire delivery device, the wire can pass through the bore of the inner guide tube, from the proximal end to the distal end of the inner guide tube, and the shape of this inner guide tube eases the passage of the wire into the cavity.

It is preferred that the wire is located to extend from the first access point at the proximal surface of the surrounding tissue to the second access point at the proximal surface of the surrounding tissue via the anterior access tunnel the cavity at the distal end of the implant and the posterior access tunnel, by the provision of a wire having engagement means (e.g. a hook) on is distal end down one access tunnel and into the cavity at the distal end of the implant and the provision of a wire having corresponding engagement means (e.g. a loop) on its distal end down the other access tunnel and into the cavity at the distal end of the implant, such that the engagement means can engage with one another (e.g. the hook can engage with the loop), forming a wire that runs down both access tunnels and round the cavity at the distal end of the implant.

Therefore the invention also provides a wire kit comprising a first wire having engagement means on is distal end and a second wire having corresponding engagement means on its distal end, for example it may comprise a wire having a hook on is distal end and a wire having a loop on its distal end, or two wires each having a hook at their distal ends. Preferably the kit further comprises the wire delivery device of the invention. It may be that the kit further comprises the inner guide tube of the invention.

The invention may also provide a dislodger device for use in the event that the wire becomes stuck during cutting.

The dislodger device comprises:
an elongate body having a proximal end and a distal end, with a handle optionally being provided at the proximal end;
a dislodging portion extending outwardly from the elongate body, the dislodging portion being located closer to the distal end of the elongate body than the proximal end of the elongate body, the dislodging portion having a curved smooth outer surface, the outer surface having a convex curvature, such that in the event the wire become stuck as it travels up the medial or lateral face of the implant, the dislodging portion can be provided to resent its curved surface and the wire can ride over the curved surface.

The elongate body suitably has a diameter that is equal to or slightly less than the minimum diameter of the access tunnel. For example its diameter may be less than the minimum diameter of the access tunnel by 1 mm or less, e.g. from 0.1 to 0.5 mm.

Essentially, the curved surface of the dislodging portion allows the wire to be moved away from any sections at the medal or lateral face that are not conducive to being cut, and towards cancellous bone that the wire can cut through.

Alternate Fifth Step

The alternate fifth stage of the procedure involves removing bony ingrowth located at the antro-lateral edge of the implant, at the antro-medial edge of the implant, at the postro-lateral edge of the implant and at the postro-medial edge of the implant. The intention of this step is to remove bony ingrowth from sections of both the medial and lateral aspects of the implant. Therefore the medial surface of the implant is cleared of bony ingrowth at or near to where it adjoins the anterior surface of the implant and at or near to where it adjoins the posterior surface of the implant. The lateral surface of the implant is cleared of bony ingrowth at or near to where it adjoins the anterior surface of the implant and at or near to where it adjoins the posterior surface of the implant. This stage may be carried out using the medial-lateral clearance device of the invention (or a set of two or more medial-lateral clearance devices according to the invention).

The medial-lateral clearance device of the invention comprises:
an elongate body having a proximal end that is provided with a handle and having a distal end that is blunt, the elongate body being in the shape of a flat plate that extends from a first elongate edge to a second elongate edge;
a cutting portion extending outwardly from the elongate body and located at or near the distal end, the cutting portion being in the shape of a flat plate that extends from an inner elongate edge, which connects with the first elongate edge of the elongate body at a substantially 90 degree angle, wherein the flat plate is further defined by a blunt edge that is located towards the distal end of the elongate body and a cutting edge that is located towards the proximal end of the elongate body;

such that the medial-lateral clearance device can be located in an access tunnel, with its flat plate elongate body in said tunnel and the flat plate cutting portion located alongside and substantially parallel to the surface of the implant, and can be moved towards the distal end of the implant until the flat plate cutting portion is completely located in a cavity at the distal end of the implant that extends in the medial and lateral directions, and the device can then be rotated by ninety degrees, such that the flat plate elongate body is located alongside and substantially parallel to the surface of the implant, with the flat plate cutting portion extending beneath the implant, and the flat plate elongate body can then be moved in a direction parallel to the surface of the implant until the flat plate cutting portion is aligned with either the medial or lateral surface of the implant, such that the medial-lateral clearance device can then be withdrawn posteriorly, with the flat plate elongate body alongside the anterior or posterior surface and the flat plate cutting portion alongside the medial or lateral surface, such that as the device is withdrawn the cutting edge of the device cuts away bony ingrowth located at said medial or lateral surface of the implant.

Preferably, a medial-lateral clearance kit is provided that comprises one or more medial-lateral clearance device where the flat plate cutting portion is ninety degrees clockwise from the flat plate elongate body and one or more medial-lateral clearance device where the flat plate cutting portion is ninety degrees anticlockwise from the flat plate elongate body.

The elongate body of the medial-lateral clearance device is a flat plate that suitably has a width that is equal to or slightly less than the diameter of the access tunnel. For example its width may be less than the diameter of the access tunnel by 1 mm or less, e.g. from 0.1 to 0.5 mm. In one embodiment, its width is from 1.5 to 6 mm, such as from 2 to 5 mm or from 2.5 to 4 mm, e.g. about 3 mm.

As the elongate body is in the form of a plate, its depth (thickness) will be less than its width. In one embodiment its depth is less than or equal to half of its width. In one embodiment the depth of the plate is from 0.2 to 2 mm, such as from 0.5 to 1.5 mm, preferably from 1 to 1.5 mm.

The elongate body may have a distal end that is angled. In one embodiment the distal end is angled upwardly from its first elongate edge to its second elongate edge, i.e. from the edge that adjoins the cutting portion to the edge that does not adjoin the cutting portion. The angle may, for example, be from 10 to 70 degrees to the elongate axis of the elongate body; preferably from 15 to 60 degrees to the elongate axis of the elongate body, such as from 20 to 45 degrees.

The cutting portion extends outwardly from the elongate body at or near the distal end of the elongate body. In this regard, the point at which the cutting edge adjoins the elongate body may, for example, be located at a distance from the distal end of from 1 to 20 mm, such as from 1.5 to 15 mm or from 1.5 to 10 mm; preferably it is at a distance from the distal end of from 2 to 10 mm, such as from 2 to 9 mm or from 2.5 to 8 mm, e.g. from 3 to 7 mm.

The cutting edge may have any suitable length. In one embodiment its width is from 1.5 to 6 mm, such as from 2 to 5 mm or from 2.5 to 4 mm, e.g. about 3 mm.

In one embodiment the distance from the first elongate edge of the elongate body to the outermost tip of the cutting edge, when measured in a direction that is perpendicular to the elongate axis of the elongate body, is the same or substantially the same (e.g. within ±5%, or within manufacturing tolerances) as the width of the flat plate elongate body.

The cutting edge may be angled upwardly, e.g. at an angle of from 20 to 70 degrees to the elongate axis of the elongate body; preferably from 30 to 60 degrees to the elongate axis of the elongate body, such as from 40 to 50 degrees.

The blunt edge may also be angled upwardly. The angle may, for example, be from 10 to 70 degrees to the elongate axis of the elongate body; preferably from 15 to 60 degrees to the elongate axis of the elongate body, such as from 20 to 45 degrees. In one embodiment the blunt edge has the same angle as the distal end of the elongate body.

The cutting edge may be straight or may be curved. If it is curved, its angle to the elongate axis should be seen as the angle created when considering the notional straight line between the distal end and the proximal end of the cutting edge with respect to the elongate axis.

The blunt edge may be straight or may be curved. If it is curved, its angle to the elongate axis should be seen as the angle created when considering the notional straight line between the distal end and the proximal end of the blunt edge with respect to the elongate axis.

As the cutting portion is in the form of a plate, its depth (thickness) will be less than its width. In one embodiment the depth of the plate is from 0.2 to 2 mm, such as from 0.5 to 1.5 mm, preferably from 1 to 1.5 mm.

In one embodiment the cutting portion is replaceably secured to the elongate body, therefore allowing the cutting portion to be removed and replaced when the cutting edge is not sharp enough for continued use.

In another embodiment the cutting portion is not replaceable and therefore the medial-lateral clearance device is simply disposed of once the cutting edge is not sharp enough for continued use.

As noted above, there would normally be provided a "left handed" and a "right handed" version of the device, i.e. a medial-lateral clearance device where the flat plate cutting portion is ninety degrees clockwise from the flat plate elongate body and a medial-lateral clearance device where the flat plate cutting portion is ninety degrees anticlockwise from the flat plate elongate body.

In addition, a set of two or more different sized devices according to the invention may be used. Thus for both the "left handed" and the "right handed" version, two or more different sizes may be provided. These may suitably differ in terms of the length of the cutting edge (distance between the distal end and the proximal end of the cutting edge). Therefore within the set each "left handed" and each "right handed" version may be provided with a length of cutting edge that is greater than the one that is the size below, e.g. the length of cutting edge may be 1 mm more than the size below, or 2 mm more, such as from 1 mm to 5 mm longer.

Therefore the smallest size of cutting edge can be used first, e.g. that may be 1 mm to 4 mm long, such as 3 mm. Then a larger size of cutting edge may be used, e.g. that may be 4 mm to 7 mm long, such as 5 mm or 6 mm. There may be two different sizes, or three different sizes, or more.

It will be appreciated that a surgical kit may be provided that comprises any combination of two or more of the novel items discussed above. Thus there may be provided a kit comprising two or more of (and in particular three or more of, or four or more of, or all of):

a targeting kit of the invention
an osteotome device of the invention
a curette device of the invention
a medial-lateral cavity maker device of the invention
a wire delivery device of the invention, or a medial-lateral clearance device of the invention.

It may be that where the surgical kit includes the targeting kit, this is provided in combination with an extra medullary targeting device, as described above.

It may be that where the surgical kit includes the osteotome device, this is in the form of a set of osteotome devices as described above.

It may be that where the surgical kit includes the medial-lateral cavity maker device, this is in the form of a set of medial-lateral cavity maker devices as described above.

It may be that where the surgical kit includes the medial-lateral clearance device, this is in the form of a pair of "left handed" and "right handed" devices as described above. Further, it may be that this is in the form of a set of different sized devices, with there being two or more different sizes for the "left handed" device and two or more different sizes for the "right handed" device.

It may be that where the surgical kit includes the wire delivery device, this is provided in combination with the inner guide tube of the invention.

It may be that the surgical kit also includes the wire kit of the invention.

It may be that the surgical kit also optionally includes the dislodger device of the invention.

DESCRIPTION OF THE DRAWINGS

The invention will now be further described with reference to the drawings, which are exemplary of the invention rather than limiting, and in which:

FIG. 1b is a medial side view of the targeting kit of the invention

FIG. 1c is an antro-lateral perspective view of the targeting kit of the invention FIG. 1f is a perspective view of an extra medullary targeting device that can be used with the kit of FIGS. 1a-1e FIG. 1g is a further perspective view of the device of FIG. 1f, in a configuration where the distance between the checking guide members has been slidably increased FIG. 2c is an antro-medial perspective view of the alternate targeting kit of the invention FIG. 2d is a perspective view of the mounting arrangement section of the alternate targeting kit of the invention FIG. 2e a is a perspective view of the holding arrangement section of the alternate targeting kit of the invention FIG. 4a is a plan view of a first curette device of the invention FIG. 4b is a plan view of an alternate curette device of the invention FIG. 4c is a plan view of a further alternate curette device of the invention FIG. 6a is a plan view of a medial-lateral clearance device of the invention, FIG. 6b is a further plan view of the medial-lateral clearance device of the invention, having been rotated 90 degrees as compared to FIG. 6a FIG. 6c is a cross sectional view of the distal end of the medial-lateral clearance device of FIG. 6a FIG. 7a is a plan view of a wire delivery device of the invention, including a detail of the guide in plan and perspective view FIG. 7d is a perspective view of the inner guide tube of the invention FIG. 9 is a plan view of a dislodger device of the invention.

All values given in the description below in terms of dimensions for the products are not limited solely to the specific embodiments as illustrated. Instead, it will be appreciated that the dimensions as mentioned also apply to the broader definitions of each product as given above.

Figure 1A:
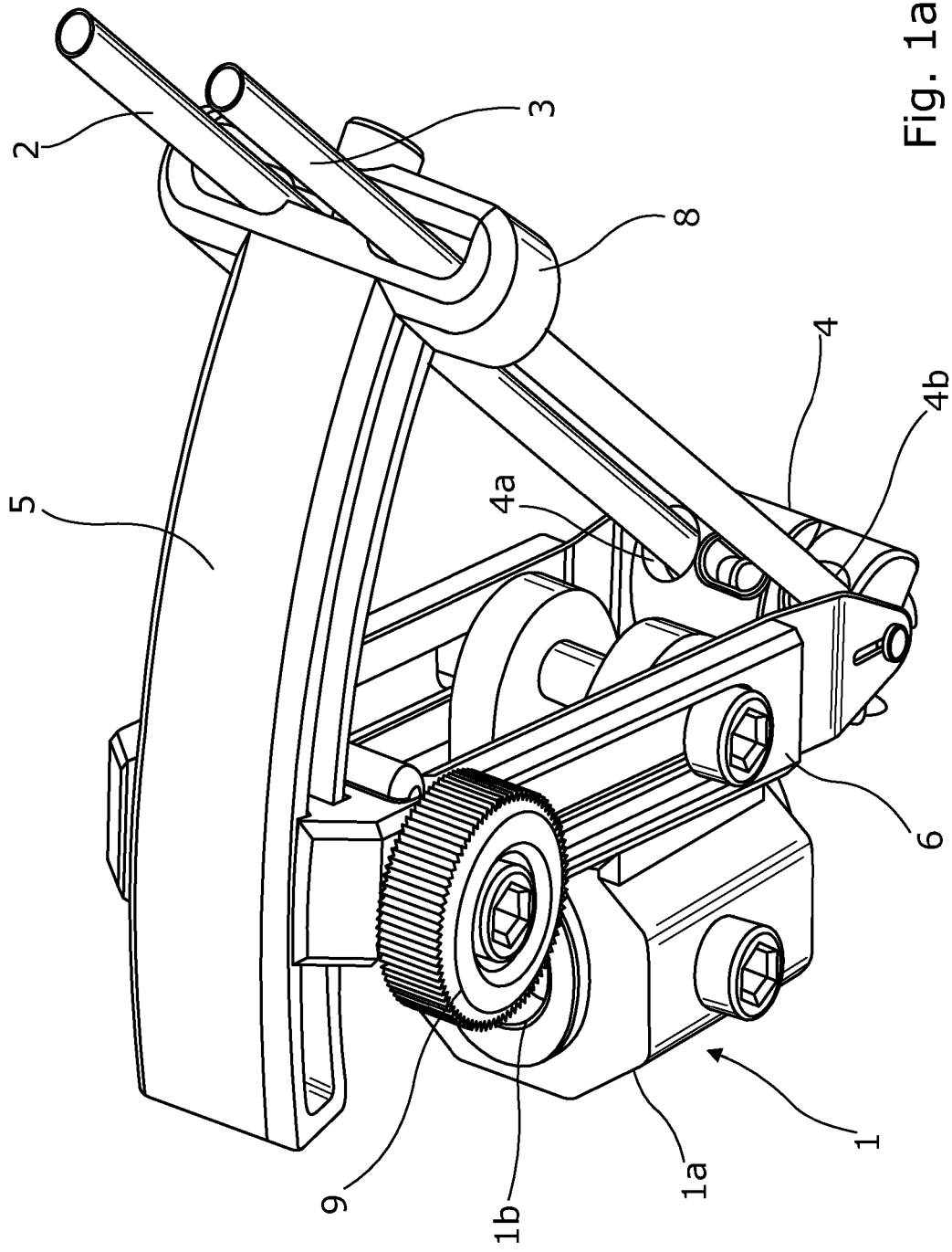
FIG. 1a is a postro-medial perspective view of a targeting kit of the invention
Figure 1D:
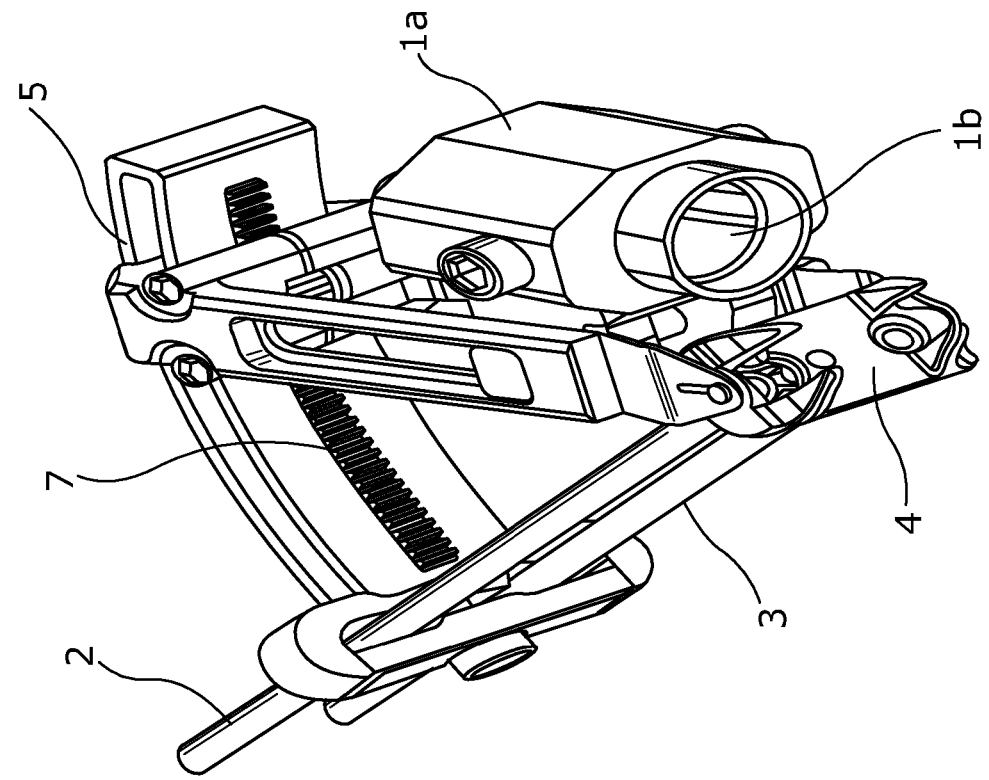
FIG. 1d is an antro-medial perspective view of the targeting kit of the invention
Figure 1E:
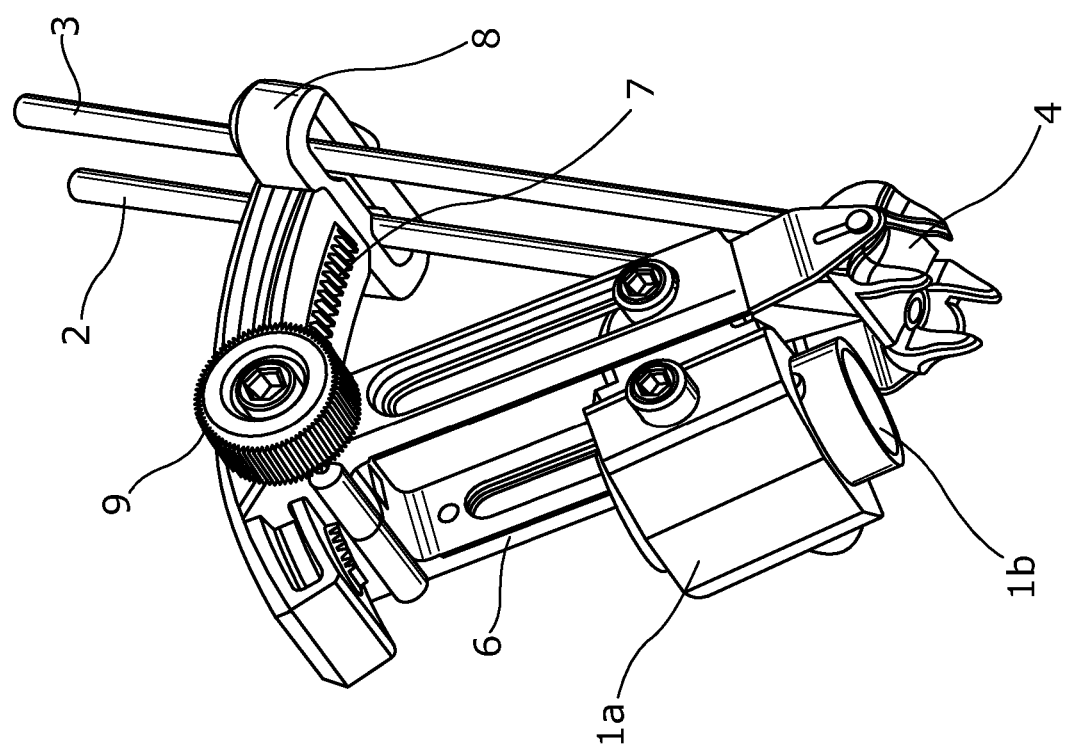
FIG. 1e is a perspective view from below of the targeting kit of the invention

The targeting kit of the invention is shown in FIG. 1.

The targeting kit comprises a mounting arrangement 1 for releasably mounting the targeting kit on the head of a femoral implant 6, first guide member 2 and second guide member 3, a holding arrangement 4 for holding the first and second guide members, and a bridging arrangement 5 between the mounting arrangement and the first and second guide members, to space the first and second guide members from the mounting arrangement.

The mounting arrangement 1 comprises a clamping component which is a jig 1a with a central elongate bore 1b. The jig can be adjusted between a position where the bore can be accessed and can receive a neck of a femoral implant, and a position where the jig is clamped shut and therefore the neck of the femoral implant that is located within the bore is secured therein. The clamping component is locked in this closed configuration during use of the apparatus.

The first guide member 2 and second guide member 3 are both elongate in shape, with a bore running along the longitudinal axis, with each guide member being able to receive a drill bit through its bore due to the bore diameters being sized to substantially correspond to the diameter of access tunnels that will be created.

The holding arrangement 4 is adjustable between a release condition, in which the positions of the first and second guide members are adjustable relative to each other, and a holding condition, in which the first and second guide members are held by the holding arrangement in a fixed position relative to each other.

The guide members 2 and 3 are secured to the holding arrangement 4 by the use of securing bores 4a, 4b in the holding arrangement 4 that are shaped and sized to receive the guide members.

The holding arrangement 4 comprises a body portion that can be located on the shoulder of the implant. The first of the securing bores is located at a distal end of the body portion and can be located against the anterior surface of the implant when the body portion is located on the shoulder of the implant. The second of the securing bores is located at a proximal end of the body portion and can be located against the posterior surface of the implant when the body portion is located on the shoulder of the implant. The distance between the bores can be adjusted, set and locked.

This body portion has two parts. The first part includes the first of the securing bores and the second part includes the second of the securing bores. The first part and second part of the body portion can be connected together to form the body portion. In this regard, the first part and second part can be connected together to provide a desired separation between the securing bores.

The bridging arrangement 5 is adjustable between a release condition, in which the position and angle of the mounting arrangement 1 is adjustable relative to the first and second guide members 2,3, and a holding condition, in which the first and second guide members 2,3 are fixedly spaced and angled from the mounting arrangement 1 by the bridging arrangement 5.

In this regard, the bridging arrangement 5 permits the mounting arrangement 1 and the first and second guide members 2,3 to be pivotably adjustable relative to each other by use of a ratchet and pinion system 7, such that the angle between the mounting arrangement 1 and the first and second guide members 2,3 can be increased or decreased as required.

The mounting arrangement 1 is attached to a first mounting base 6, and the first mounting base 6 is connected to the ratchet and pinion system 7. The first and second guide members 2,3 are attached to a second mounting base 8, and the second mounting base 8 is connected to the ratchet and pinion system 7.

In this regard, the first mounting base 6 pivotably moves with respect to the second mounting base 8 via the ratchet and pinion system 7, thereby altering the angle between the mounting arrangement 1 and the first and second guide members 2,3. In this regard, the second mounting base 8 is fixedly connected to the ratchet and pinion system 7, whilst the first mounting base 6 is moveably connected to the ratchet and pinion system 7.

The pivoting movement is about a pivot point which is a ball joint, e.g. a restricted articulation ball joint.

The first mounting base 6 connects the bridging arrangement 5 to both the mounting arrangement 1 and the holding arrangement 4. This first mounting base 6 connects with the holding arrangement 4 at or near the pivot point about which the relative pivotal movement of the mounting arrangement 1 and the first and second guide members 2,3 occurs.

The pivoting movement via the ratchet and pinion system can be effected by the user via the use of thumb wheel 9.

The bridging arrangement 5 includes a locking mechanism for locking the mounting arrangement 1 relative to the first and second guide members 2,3 once they are at the desired angle to each other.

Thus the relative positions of the first and second guide members 2, 3 and the mounting arrangement 4, both in terms of their distance apart and angle to one another, can be adjusted as required.

Therefore in the targeting kit the mounting arrangement 1 can be secured onto the shoulder of the implant, with the neck of the implant in the bore 1*b*, with the first and second guide members 2 and 3 being located on the shoulder of the implant, with the first guide member 2 located at the anterior of the implant and the second guide member 3 located at the posterior of the implant, the first guide member 2 being angled such that its longitudinal axis is spaced from and substantially parallel to the anterior surface of the implant and the second guide member 3 being angled such that its longitudinal axis is spaced from and substantially parallel to the posterior surface of the implant.

The targeting kit may be used in combination with an extra medullary targeting device as shown in FIG. 1*f* and 1*g*.

The extra medullary targeting device comprises a targeting kit interlocking portion 121. This targeting kit interlocking portion 121 comprises a first guide member interlocking component 121*a*, which comprises a bore within which the first guide member 2 of the targeting kit can be received. The targeting kit interlocking portion 121 also comprises a second guide member interlocking component 121*b*, which comprises a locking pin 123 that can be received in the bore of the second guide member 3 of the targeting kit. The elongate axis of the locking pin 123 is parallel to the longitudinal axis of the bore of the first guide member interlocking component 121*a*.

The extra medullary targeting device also comprises an extra medullary guidance portion 122. The extra medullary guidance portion 122 comprises a bore within which a test pin 124 having an elongate body can be received.

The extra medullary targeting device also comprises a holding arrangement 125 for holding and spacing the targeting kit interlocking portion and the extra medullary guidance portion 121,122. This holding arrangement holds the portions 121, 122 fixedly relative to each other in terms of their angle, such that the bore of the first guide member interlocking component and the bore of the extra medullary guidance portion have their longitudinal axes aligned, such that these bores run parallel to each other. However, the holding arrangement is adjustable in terms of the distance between the two portions. In this regard, the holding arrangement 125 is adjustable between a release condition, in which the distance between the two portions is adjustable, and a holding condition, in which the distance between the two portions is fixed.

The locking pin may have a length of elongate body that is from 30 to 100 mm; for example it may be a length between 40 and 80 mm.

The test pin may have a length of elongate body that is from 70 to 250 mm; for example it may be a length between 100 and 200 mm.

The distance between the portions 121, 122 may be from 30 to 60 mm; for example the distance may be adjustable from a minimum of 34 mm up to a maximum of 52 mm. When reference is made to the distance between the portions this is measured as the distance between the bore that receives the locking pin and the bore that receives the test pin.

The holding arrangement 125 has two parts. The first part includes the portion 121 and the second part includes the portion 122. The first part and second part can be connected together to form the holding arrangement. The first part and second part may be connected together to provide a desired separation between the checking guide members.

Each body part has an interlocking section extending therefrom, wherein each interlocking section has an elongate aperture, such that the two body parts can be fixed at a desired distance to each other by using a fastening member 126, such as a bolt, to extend through both elongate apertures and fix them together.

By selecting the position within the elongate apertures where the fastening member 126 is located, different separation distances can be achieved, as can be seen by reference to FIGS. 1*f* and 1*g* where different separation distances are shown.

Accordingly, the bore of the first guide member interlocking component 121*a* can receive the first guide member 2 of the targeting kit, and the locking pin 123 of the second guide member interlocking component 121*b* can be received in the bore of the second guide member 3 of the targeting kit. The test pin 124 can be received within the bore of the extra medullary guidance portion 122. Therefore the bore of the first guide member interlocking component 121*a* is angularly aligned with the first guide member 2 of the targeting kit, and the locking pin 123 of the second guide member interlocking component 121*b* is angularly aligned with the second guide member 3 of the targeting kit. Consequently, the test pin 124 located in the bore of the extra medullary guidance portion 122 is also angularly aligned with the first and second guide members 2, 3 of the targeting kit.

The test pin 124 will lie outside the femur. This test pin reflects the alignment of the guide members 2,3 of the targeting kit. The test pin 124 and the guide members 2,3 of the targeting kit all lie in the saggital plane.

Due to the fact that this test pin extends outside the patient's body, the alignment of the test pin can be checked, e.g. with reference to the location of the distal tip of implant, as determined via x-ray, or with reference to the middle of the medio-lateral diameter of the femur at the level of the distal tip of the implant. It can be ensured that the test pin is pointing in that direction, and thus that the guide members 2,3 of the targeting kit are also pointing in that direction.

Accordingly, this provides a double check that the guide members 2,3 are correctly aligned before drill bits are used in these guide members to drill the access tunnels.

Figures 2A, 2B:
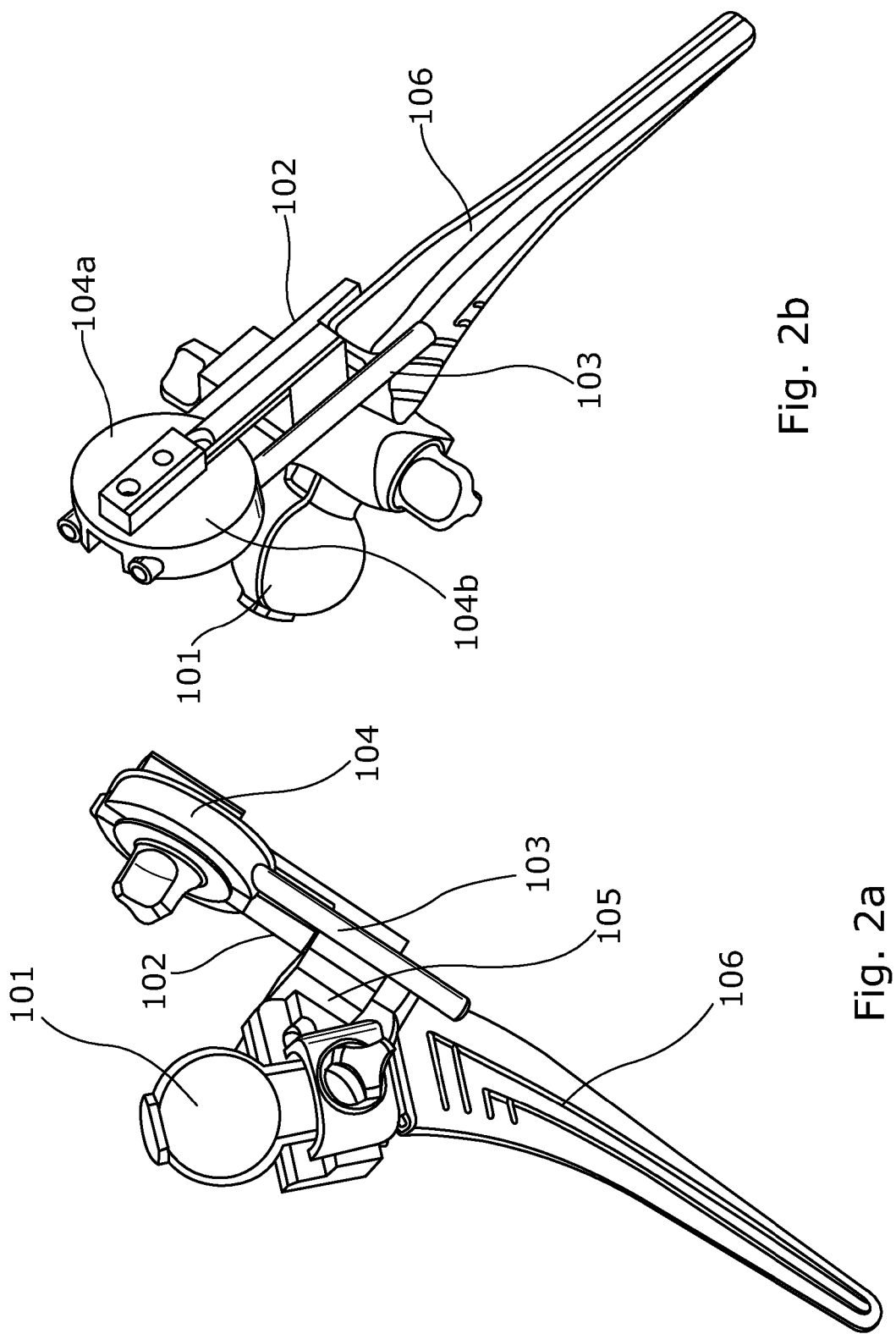
FIG. 2a is a postro-medial perspective view of an alternate targeting kit of the invention
FIG. 2b is a postro-lateral perspective view of the alternate targeting kit of the invention

An alternate targeting kit of the invention is shown in FIG. 2.

The targeting kit comprises a mounting arrangement 101 for releasably mounting the targeting kit on the head of a femoral implant 106, first guide member 102 and second guide member 103, a holding arrangement 104 for holding the first and second guide members, and a bridging arrangement 105 between the mounting arrangement and the first and second guide members, to space the first and second guide members from the mounting arrangement.

The mounting arrangement 101 comprises a cup-shaped component. This cup-shaped component is sized and shaped to be able to fit round and engage with part of the head of a femoral implant.

The first guide member 102 and second guide member 103 are both elongate in shape, with a bore running along the longitudinal axis, with each guide member being able to receive a drill bit through its bore due to the bore diameters being sized to substantially correspond to the diameter of access tunnels that will be created.

The holding arrangement 104 is adjustable between a release condition, in which the positions of the first and second guide members are adjustable relative to each other, and a holding condition, in which the first and second guide members are held by the holding arrangement in a fixed position relative to each other.

The guide members 102 and 103 are secured to the holding arrangement 104 by the use of securing bores in the holding arrangement 104 that are shaped and sized to receive the guide members.

The holding arrangement 104 comprises two body portions 104a and 104b, each of which includes one of the securing bores that can be used to hold one of the guide members 102 and 103.

Each body portion 104a, 104b has an interlocking section extending therefrom, wherein each interlocking section has an elongate aperture, such that the two body portions can be fixed at a desired distance and angle to each other by using a fastening member, such as a bolt, to extend through both elongate apertures and fix them together.

By selecting the position within the elongate apertures where the fastening member is located, different separation distances and angles can be achieved.

The provision of the elongate apertures therefore allows the relative positions of the two body portions, both in terms of their distance apart and angle to one another, to be adjusted as required. Thus the relative positions of the securing bores can be adjusted.

The distance between the guide members can of course be adjusted by adjusting the distance between the securing bores, and the angle between the guide members can be adjusted by adjusting the angle between the securing bores.

The bridging arrangement 105 is adjustable between a release condition, in which the position of the mounting arrangement 101 is adjustable relative to the first and second guide members 102 and 103, and a holding condition, in which the first and second guide members are fixedly spaced from the mounting arrangement by the bridging arrangement.

The bridging arrangement permits the mounting arrangement 101 and the first and second guide members 102,103 to be slidably adjustable relative to each other, such that the distance between the mounting arrangement and the first and second guide members can be increased or decreased as required, and to be pivotably adjustable relative to each other, such that the angle between the mounting arrangement and the first and second guide members can be increased or decreased as required.

The bridging arrangement 105 includes an elongate aperture 105a and a fastening member 105b that can extend through the elongate aperture and be secured thereto.

The elongate aperture 105a is linked to the first and second guide members via the holding arrangement 104 and the fastening member 105b is linked to the mounting arrangement 101. The fastening member can extend through the elongate aperture and can then be secured in position, fixing the elongate aperture and the fastening member together.

By selecting the position within the elongate aperture where the fastening member is located, different separation distances and angles can be achieved.

Thus the relative positions of the first and second guide members 102, 103 and the mounting arrangement 104, both in terms of their distance apart and angle to one another, can be adjusted as required.

Therefore in the targeting kit the mounting arrangement 101 can be secured onto the head of the implant, with the first and second guide members 102 and 103 being located on the shoulder of the implant, with the first guide member 102 located at the anterior of the implant and the second guide member 103 located at the posterior of the implant, the first guide member 102 being angled such that its longitudinal axis is spaced from and substantially parallel to the anterior surface of the implant and the second guide member 3 being angled such that its longitudinal axis is spaced from and substantially parallel to the posterior surface of the implant.

The osteotome device of the invention is shown in FIG. 3. The device comprises an elongate body 11, having a proximal end 11a that is provided with a handle 11d and a distal end 11b that is blunt, and a cutting portion 14.

The elongate body 11 includes a distal section 12 extending from the distal end 11b to a shoulder point 11c, and an indented section 13 extending from the shoulder point 11c towards the proximal end 11a. The shoulder point is located closer to the distal end than the proximal end, e.g. at a distance from the distal end of from 2.5 to 15 mm such as from 5 to 10 mm. The depth of the distal section 12 is greater than the depth of the indented section 13.

The cutting portion 14 has a front face and a back face, with the back face being attached to the indented section of the elongate body. The cutting portion 14 therefore extends from the indented section of the elongate body.

The cutting portion 14 is attached to the elongate body 11 at joint 14a. Joint 14a may, for example, be a laser welded joint.

The distance between the back face and the front face of the cutting portion is substantially the same as the difference in depth between the distal section and the indented section of the elongate body. Therefore the front face of the cutting portion does not protrude outwardly from the elongate body. This can be seen in, for example, FIG. 3e.

The front face of the cutting portion 14 is blunt but is connected to the back face by a first cutting side 15 and a second cutting side 16. The cutting portion is triangular in cross sectional shape, with two of the three sides of the triangle being the first cutting side and the second cutting side.

Therefore part of the first cutting side and part of the second cutting side angularly extend outwardly of the elongate body, providing cutting surfaces for cutting away bony ingrowth.

The triangle is an isosceles triangle, with the first cutting side and the second cutting side being the same length. The first cutting side and the second cutting side are suitably at an angle to one another of from 50 to 80 degrees, e.g. from 60 to 70 degrees.

Figure 3A:
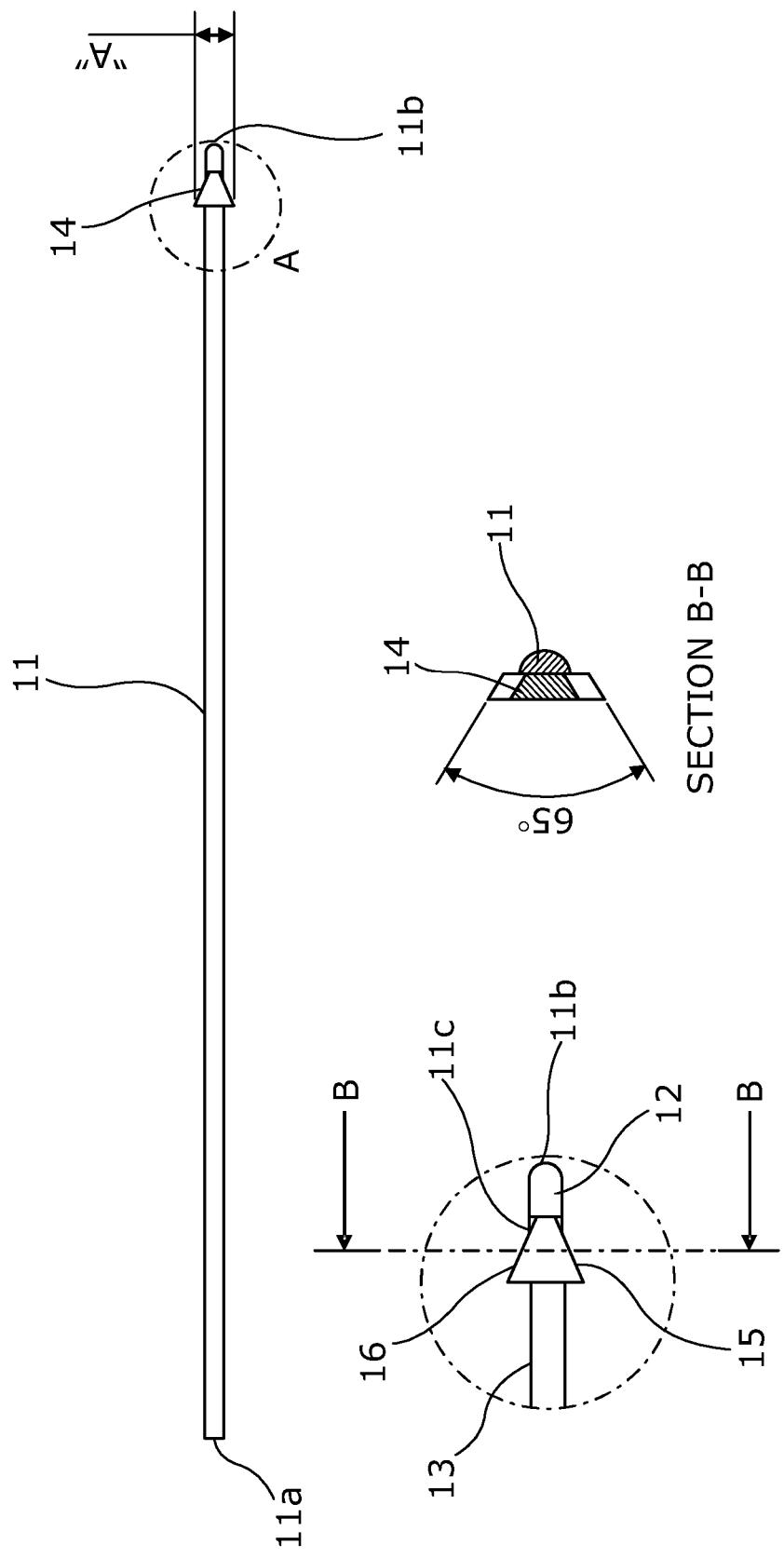
FIG. 3a is a plan view of an osteotome device of the invention, including a detail of the cutting portion and a cross section thereof
Figure 3B:
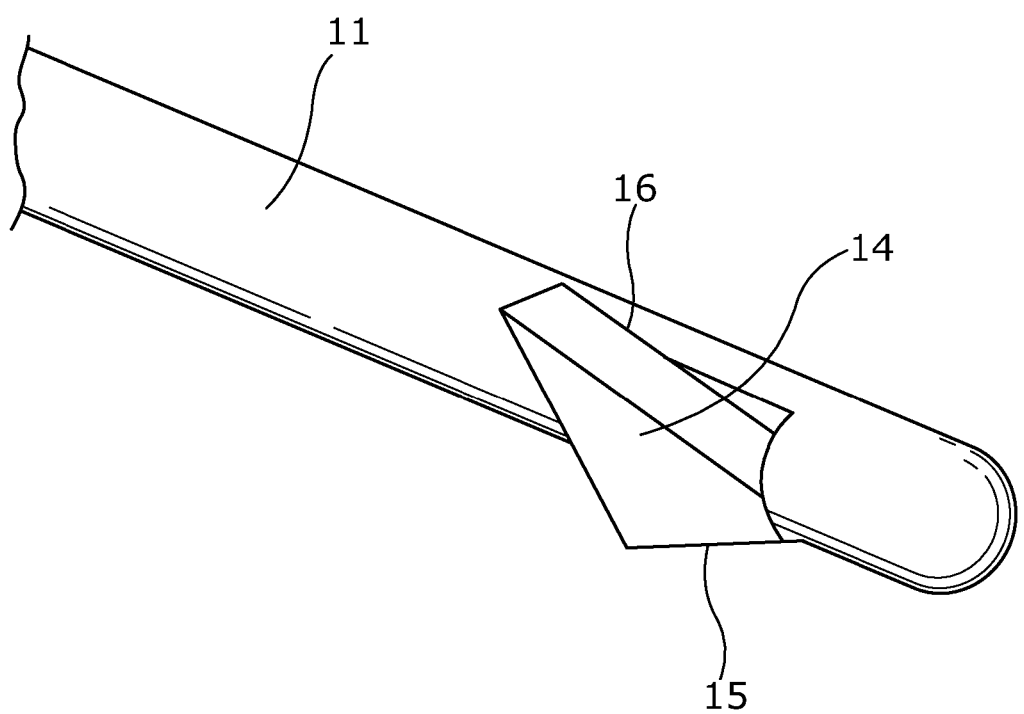
FIG. 3b is a perspective view of the osteotome device of the invention
Figure 3C:
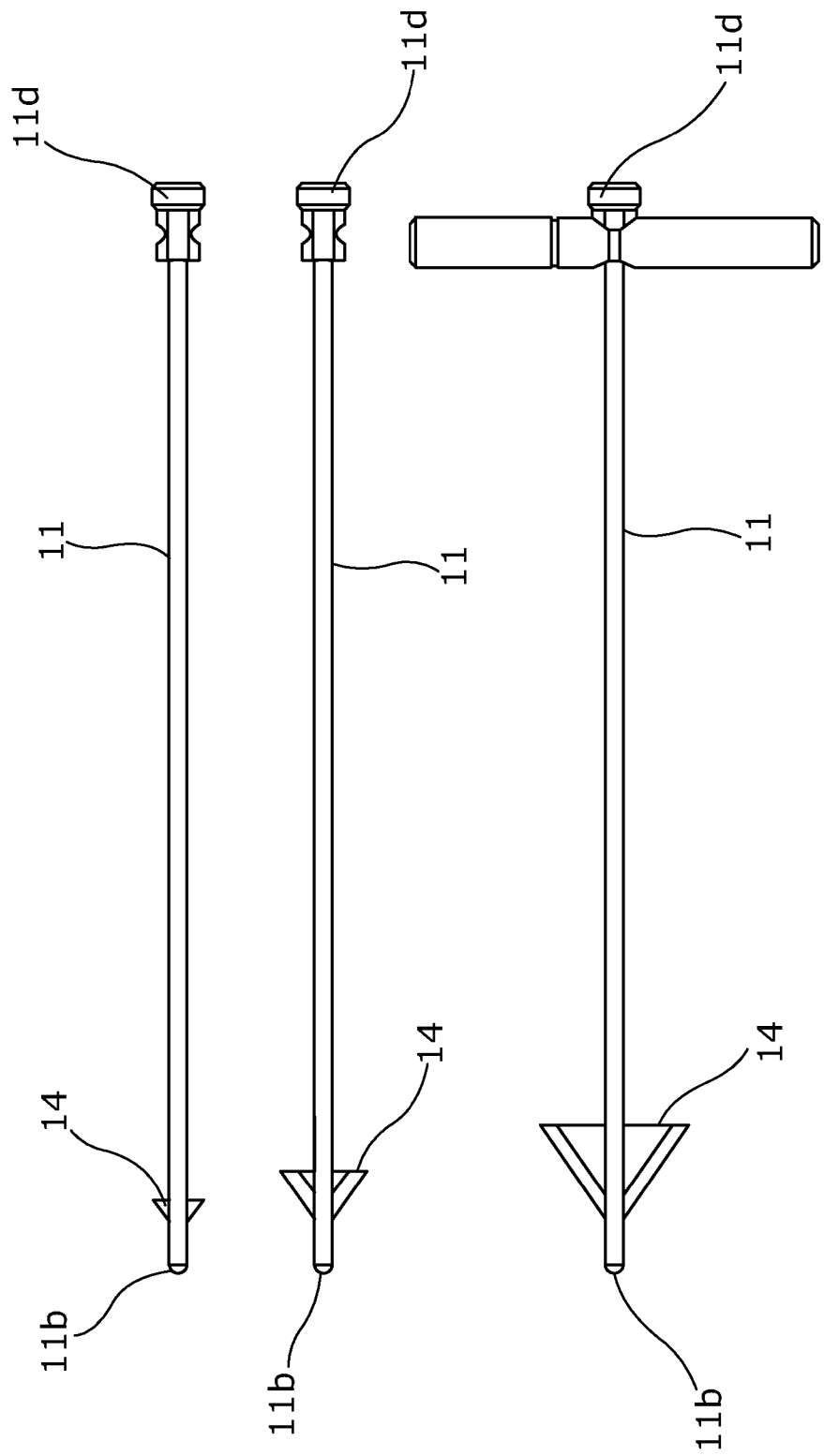
FIG. 3c is a plan view of a set of three osteotome devices of the invention, each with different sizes of cutting portion
Figures 3D, 3E:
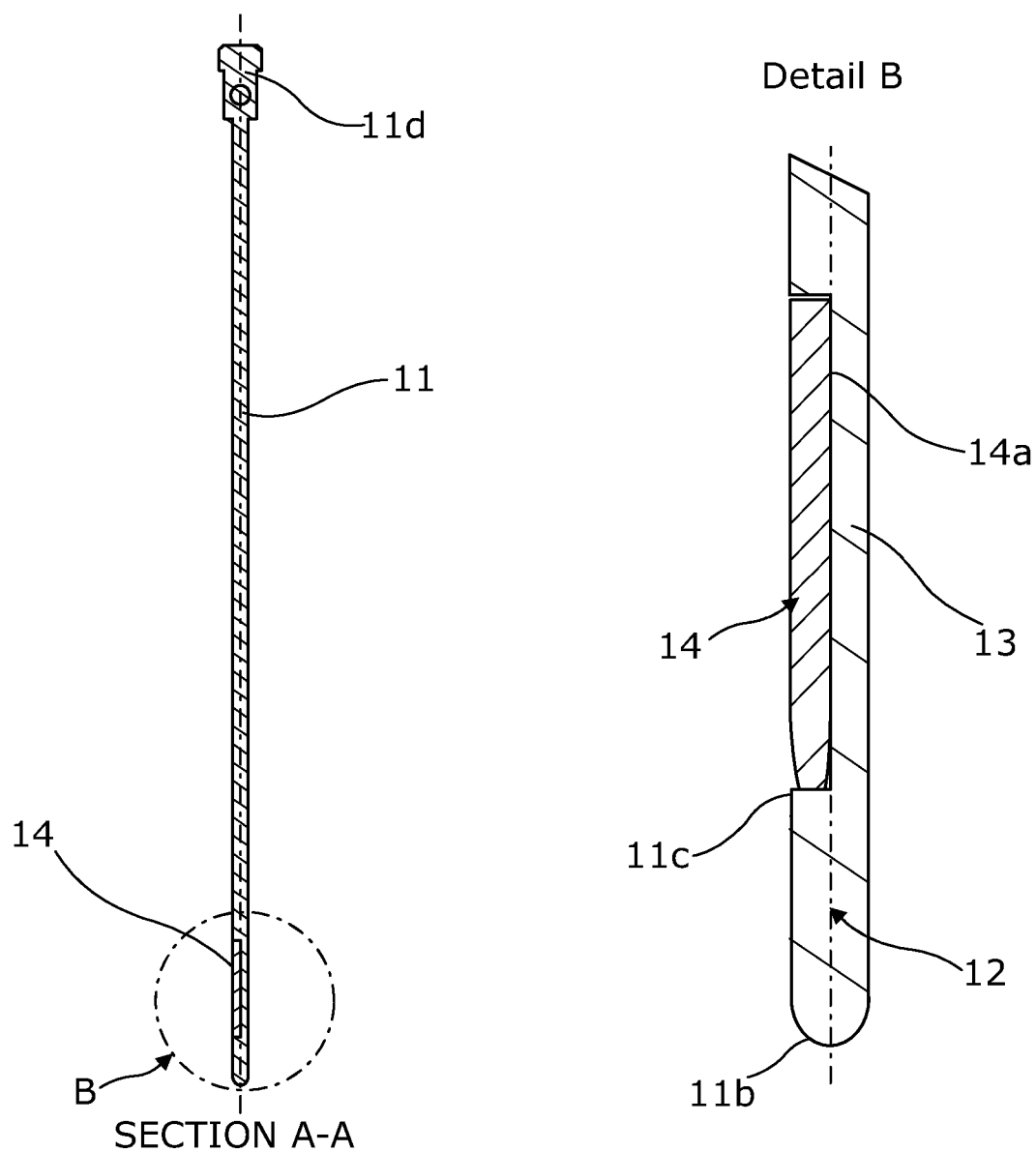
FIG. 3d is a side view of an osteotome device of the invention
FIG. 3e is a detailed view of the osteotome device shown in FIG. 3d, showing Detail B

It may be that the third side of the triangle, i.e. the non-cutting side, is any suitable width. One example of a suitable width is 25 mm. It will be appreciated that a range of different widths could be suitable, e.g. within a range of from 5 mm to 50 mm, such as from 10 mm to 40 mm. As shown in FIG. 3c, a set of osteotomes, each having a different size of cutting portion 14, each with a different width, can be provided.

The cutting portion 14 may also have any suitable length, i.e. the distance from this non-cutting side to the tip of the cutting potion 14 (where the two cutting sides meet). One example of a suitable length is 19 mm. It will be appreciated that a range of different lengths could be suitable, e.g. within a range of from 5 mm to 50 mm, such as from 10 mm to 40 mm. As shown in FIG. 3c, a set of osteotomes, each having a different size of cutting portion 14, each with a different length, can be provided.

The osteotome device can be located in an access tunnel and pushed in the direction of the distal end of the implant so as to cut away bony ingrowth with the first cutting side and the second cutting side.

When a set of osteotomes is provided, the osteotome with the smallest size of cutting portion will be used first. This will therefore cut away a first width of bony ingrowth with the first cutting side and the second cutting side. The osteotome that is the next size up can then be used, to cut away a second, broader, width of bony ingrowth with the first cutting side and the second cutting side.

This process can then be repeated further with additional osteotomes of increasing size, in terms of the size of the cutting portion, until a channel where bony ingrowth has been cut away is achieved that has a desired size.

It will be appreciated that due to the shape of the osteotome cutting portion, the channel where bony ingrowth is cut away will be wider towards the proximal end of the implant than the distal end of the implant.

The curette device of the invention is shown in FIG. 4. The device comprises an elongate body 110 and a cutting portion 111 extending outwardly from the elongate body.

The elongate body 110 has a proximal end that is provided with a handle 110a. It also has a distal end 110b that is blunt. The elongate body 110 is in the shape of a flat plate. This extends from a first elongate edge to a second elongate edge.

In one embodiment, the width of this body 110 is from 3 to 6 mm, e.g. about 4 to 5 mm. In one embodiment the depth of this body 110 is from 0.5 to 1.5 mm, preferably from 1 to 1.5 mm.

The cutting portion 111 is located near the distal end 110b of the elongate body. This cutting portion 111 has a blunt edge 112 which is substantially parallel to the elongate axis E-E of the elongate body. The cutting portion 111 also has a cutting edge 113, which is at an angle of from 30 to 150 degrees to the elongate axis E-E of the elongate body. The cutting portion also has an attachment edge which is the edge by which the cutting portion is attached to the elongate body (at the second elongate edge).

The cutting edge 113 extends from a proximal end, where it adjoins the elongate body, to a distal end, which is away from the body. The cutting edge 113 is sharp at least at the distal end 113a. It may optionally be sharp along some or all of the remainder of its length. For example, going from the distal end towards the proximal end the first 10% or more of the length may be sharp.

In FIG. 4a the cutting edge is at an angle of about 45 degrees to the elongate axis of the elongate body.

In FIG. 4b the cutting edge is at an angle of about 135 degrees to the elongate axis of the elongate body.

In FIG. 4c the cutting edge is at an angle of about 45 degrees to the elongate axis of the elongate body.

The cutting edge may be any suitable width. One example of a suitable width is 3 mm. It will be appreciated that a range of different widths could be suitable, e.g. within a range of from 0.5 mm to 6 mm, such as from 1 mm to 4 mm. It is possible that a set of curettes, each having a different size of cutting edge, can be provided.

The distal end of the cutting edge may be any suitable distance from the elongate body. It may be that the distance from the elongate body (e.g. from its second elongate edge) to the distal end of the cutting edge, when measured in a direction that is perpendicular to the elongate axis of the elongate body, is from 4 to 9 mm, especially from 5 to 8 mm.

It is possible that a set of curettes, each having a different distance for the distal end of the cutting edge, can be provided.

The curette device can be located in an access tunnel, with its elongate axis E-E substantially aligned with the central axis running along the length of the tunnel, and with the distal end located at or near the distal (closed) end of the access tunnel. It can then be angled within that tunnel such that its elongate axis is angled with respect to the central axis running along the length of the tunnel, until the cutting edge 113 (especially the distal end 113a of said cutting edge) contacts the bony ingrowth located between the surface of the implant and the femoral cortex. The curette device can then be withdrawn from the access tunnel whilst being retained in an angled position, such that as the device is withdrawn the cutting edge 113 cuts away bony ingrowth located between the surface of the implant and the inner femoral cortex.

Figure 5A:
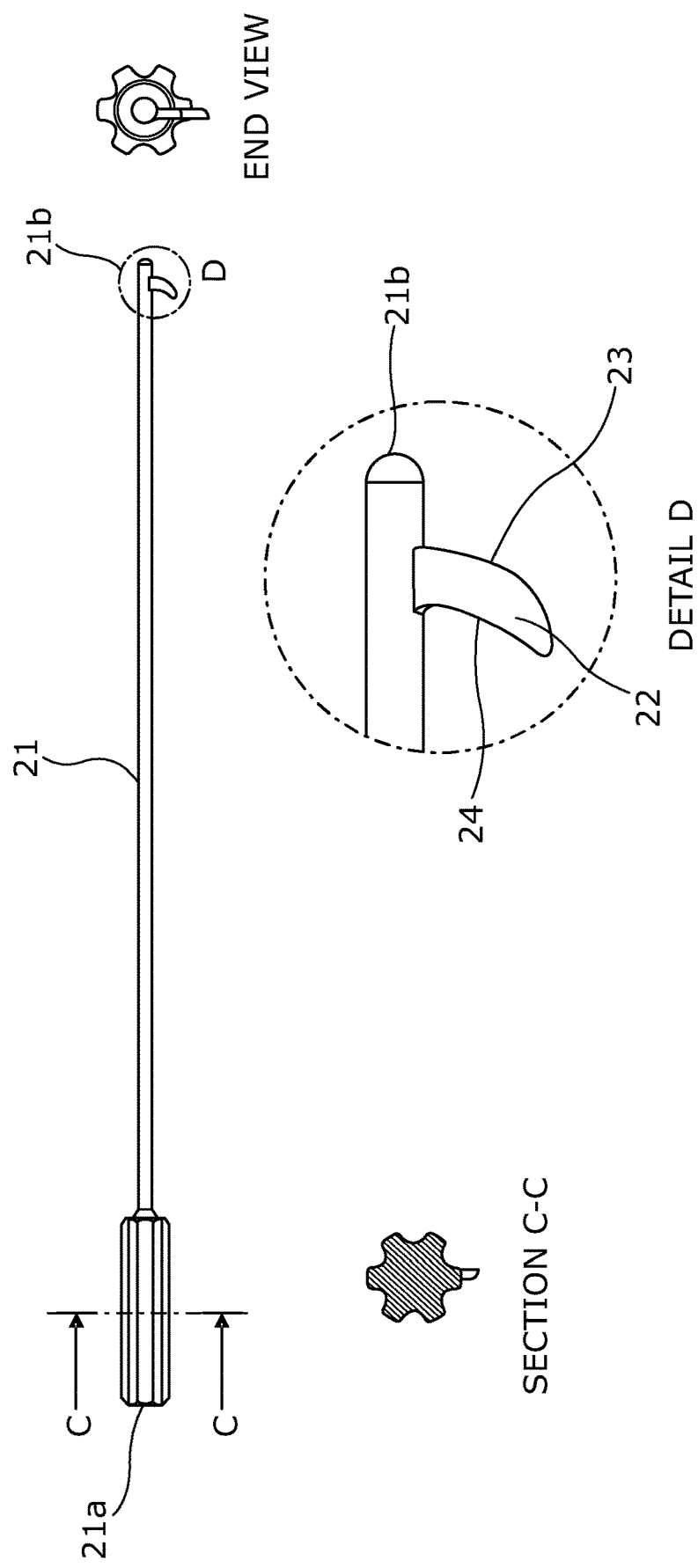
FIG. 5a is a plan view of a medial-lateral cavity maker device of the invention, including a detail of the cutting portion and an end view
Figure 5B:
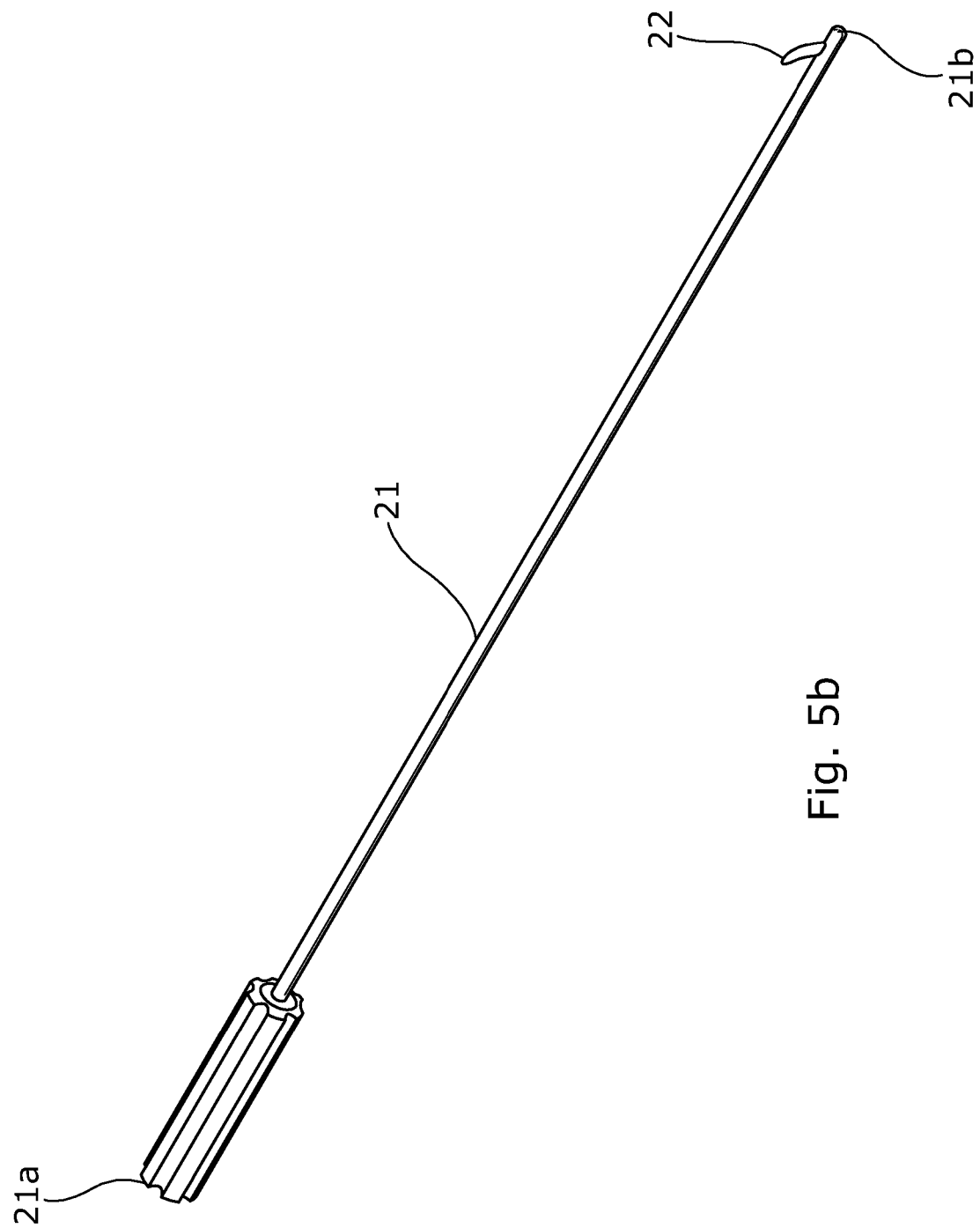
FIG. 5b is a perspective view of the medial-lateral cavity maker device of the invention
Figure 5C:
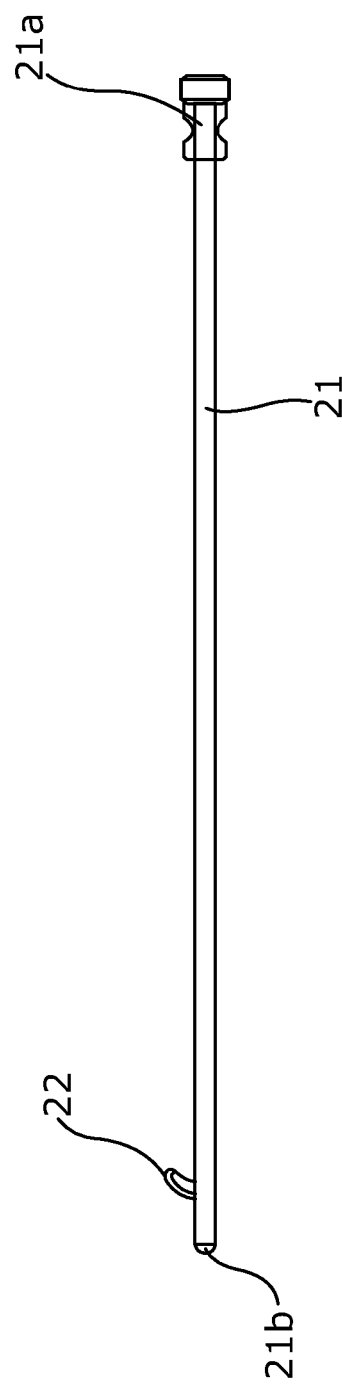
FIG. 5c is a further plan view of a medial-lateral cavity maker device of the invention

The medial-lateral cavity maker device of the invention is shown in FIG. 5.

The medial-lateral cavity maker device comprises an elongate body 21 having a proximal end 21a that is provided with a handle and a distal end 21b that is blunt; and a cutting portion 22 extending outwardly from the elongate body 21.

The cutting portion 22 is located closer to the distal end 21b of the elongate body than the proximal end 21a of the elongate body. The cutting portion may be located at a distance from the distal end of from 2 to 10 mm.

The cutting portion 22 has a connecting end attached to the elongate body and a protruding end located away from the elongate body. The connecting end and the protruding end are connected by a first edge 23 located towards the distal end of the elongate body and a second edge 24 located towards the proximal end of the elongate body.

The cutting portion 22 overall has a hook shape. The first edge 23 is blunt and is a curved edge that is convex and the second edge 24 is a cutting edge and is a curved edge that is concave.

Therefore the medial-lateral cavity maker device can be located in an access tunnel and once the cutting portion is beyond the distal end of the implant it can be rotated so as to cut away bony ingrowth with the second edge 24 at the distal end of the implant, to create a cavity at the distal end of the implant that extends in the medial and lateral directions.

The medial-lateral clearance device is shown in FIG. 6.

The medial-lateral clearance device comprises an elongate body 120 and a cutting portion 121 that extends outwardly from the elongate body.

The elongate body 120 has a proximal end that is provided with a handle 120a and a distal end 120b that is blunt. The elongate body 120 is in the shape of a flat plate that extends from a first elongate edge 120c to a second elongate edge 120d.

In one embodiment, the width of this body 120 is from 2.5 to 4 mm, e.g. about 3 mm. In one embodiment the depth of this body 120 is from 0.5 to 1.5 mm, preferably from 1 to 1.5 mm.

It can be seen that the distal end is angled upwardly from its first elongate edge to its second elongate edge. The angle may, for example, be from 20 to 45 degrees, such as about 30 degrees, to the elongate axis of the elongate body.

The cutting portion is located near the distal end 120b of the elongate body. The cutting portion 121 is in the shape of a flat plate. This extends from an inner elongate edge 121a which connects with the first elongate edge 120c of the elongate body at a substantially 90 degree angle, as can be best seen in FIG. 6c.

The depth of this flat plate cutting portion 121 is suitably from 0.5 to 1.5 mm, preferably from 1 to 1.5 mm.

The flat plate of the cutting portion is also provided with a blunt edge 122 that is located towards the distal end 120b of the elongate body.

The blunt edge is angled upwardly. The angle may, for example, be from 20 to 45 degrees, such as about 30 degrees, to the elongate axis of the elongate body.

The flat plate of the cutting portion is also provided with a cutting edge 123 that is located towards the proximal end of the elongate body.

The cutting edge may have any suitable length. In one embodiment its width is from 2 to 5 mm or from 2.5 to 4 mm, e.g. about 3 mm.

As can be seen, the cutting edge is angled upwardly, e.g. at an angle of from 30 to 60 degrees to the elongate axis of the elongate body, such as about 45 degrees.

The medial-lateral clearance device can be located in an access tunnel, with its flat plate elongate body 120 in said tunnel and the flat plate cutting portion 121 located alongside and substantially parallel to the surface of the implant. It can then be moved towards the distal end of the implant until the flat plate cutting portion 121 is completely located in a cavity at the distal end of the implant that extends in the medial and lateral directions. Within that cavity the flat plate cutting portion 121 is free to rotate. At that point the device can then be rotated by ninety degrees, such that the flat plate elongate body 120 is located alongside and substantially parallel to the surface of the implant, with the flat plate cutting portion 121 extending beneath the implant. Once this has been done the flat plate elongate body 120 can then be moved in a direction parallel to the surface of the implant until the flat plate cutting portion 121 is aligned with either the medial or lateral surface of the implant. Then the medial-lateral clearance device can be withdrawn posteriorly, with the flat plate elongate body 120 lying alongside the anterior or posterior surface and the flat plate cutting portion 121 lying alongside the medial or lateral surface. This then means that as the device is withdrawn posteriorly the cutting edge 123 of the device cuts away bony ingrowth located at said medial or lateral surface of the implant.

It will be appreciated that a pair of such medial-lateral clearance devices should be provided: one where the flat plate cutting portion is ninety degrees clockwise from the flat plate elongate body and one where the flat plate cutting portion is ninety degrees anticlockwise from the flat plate elongate body.

In addition, for both the "left handed" version and the "right handed" version, two or more different sizes may be provided. For example, for each version there may be a first size where the cutting edge is from 1.5 mm to 3.5 mm long, such as 3 mm, and a second size where the cutting edge is from 4.5 mm to 7 mm long, such as 5 mm or 6 mm.

Figure 7B:
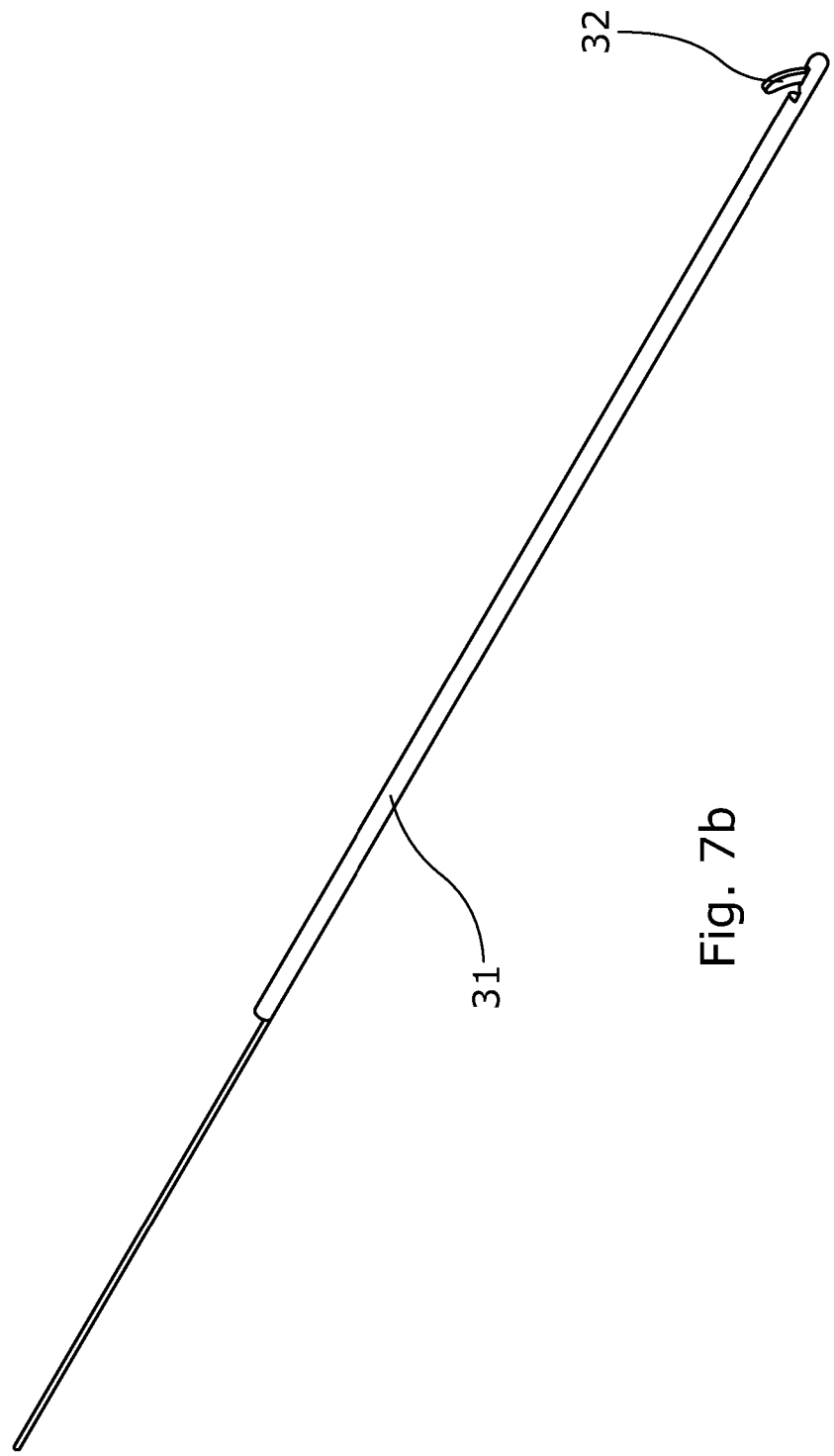
FIG. 7b is a perspective view of the wire delivery device of the invention
Figure 7C:
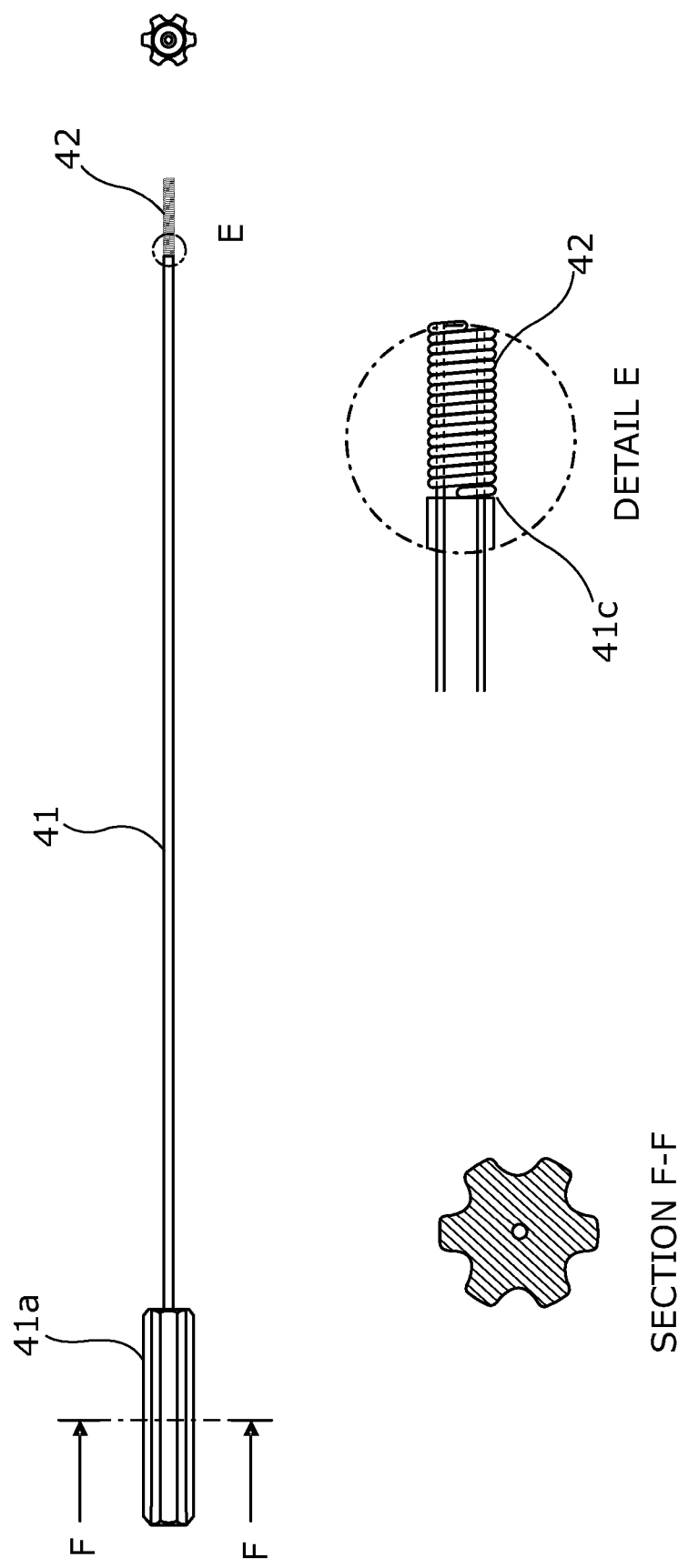
FIG. 7c is a plan view of the inner guide tube of the invention, including a detail in plan and a cross section of the proximal end

The wire delivery device of the invention is shown in FIG. 7.

The wire delivery device comprises an elongate body 31 having a proximal end 31a that is provided with a handle and a distal end 31b that is blunt and a wire guidance portion 32 extending outwardly from the elongate body.

The wire guidance portion 32 is located closer to the distal end 31b of the elongate body than the proximal end 31a of the elongate body.

The wire guidance portion 32 has a connecting end attached to the elongate body and a protruding end located away from the elongate body, the connecting end and the protruding end being connected by a first curved surface 33 and a second curved surface 34.

The wire guidance portion 32 overall has a hook shape that curves upwardly (that is, towards the proximal end rather than the distal end). Thus the first curved surface 33 is convex and is located towards the distal end of the elongate body whilst the second curved surface 34 is concave and is located towards the proximal end of the elongate body.

The elongate body has a bore 36 running from its proximal end 31a to an exit hole 35 located adjacent to the second curved surface 34 of the wire guidance portion. The exit hole 35 is aligned with the second curved surface, so that a wire exiting the exit hole directly falls onto that concave surface. The exit hole may include a notch to assist with aligning a wire exiting the exit hole 35 onto the centreline of the concave surface.

Therefore the wire delivery device can be located in an access tunnel and wire passed through the bore 36 from the proximal end to the exit hole 35, and can then be guided into the cavity at the distal end of the implant.

The inner guide tube of the invention is also shown in FIG. 7.

The inner guide tube comprises an elongate body 41 having a proximal end 41a that is provided with a handle and a distal end 41b. A flexible section 42 extends from the distal end 41b to a junction point 41c, the flexible section being formed from a spring and therefore being sufficiently flexible that the flexible section can bend so that the elongate body can form a J-shape.

The elongate body 41 has a bore running from its proximal end to its distal end, such that the inner guide tube can be located in the bore of the wire delivery device, with the flexible section 42 extending from the exit hole 35 and over the second curved surface 34 of the wire guidance portion.

Figure 8:
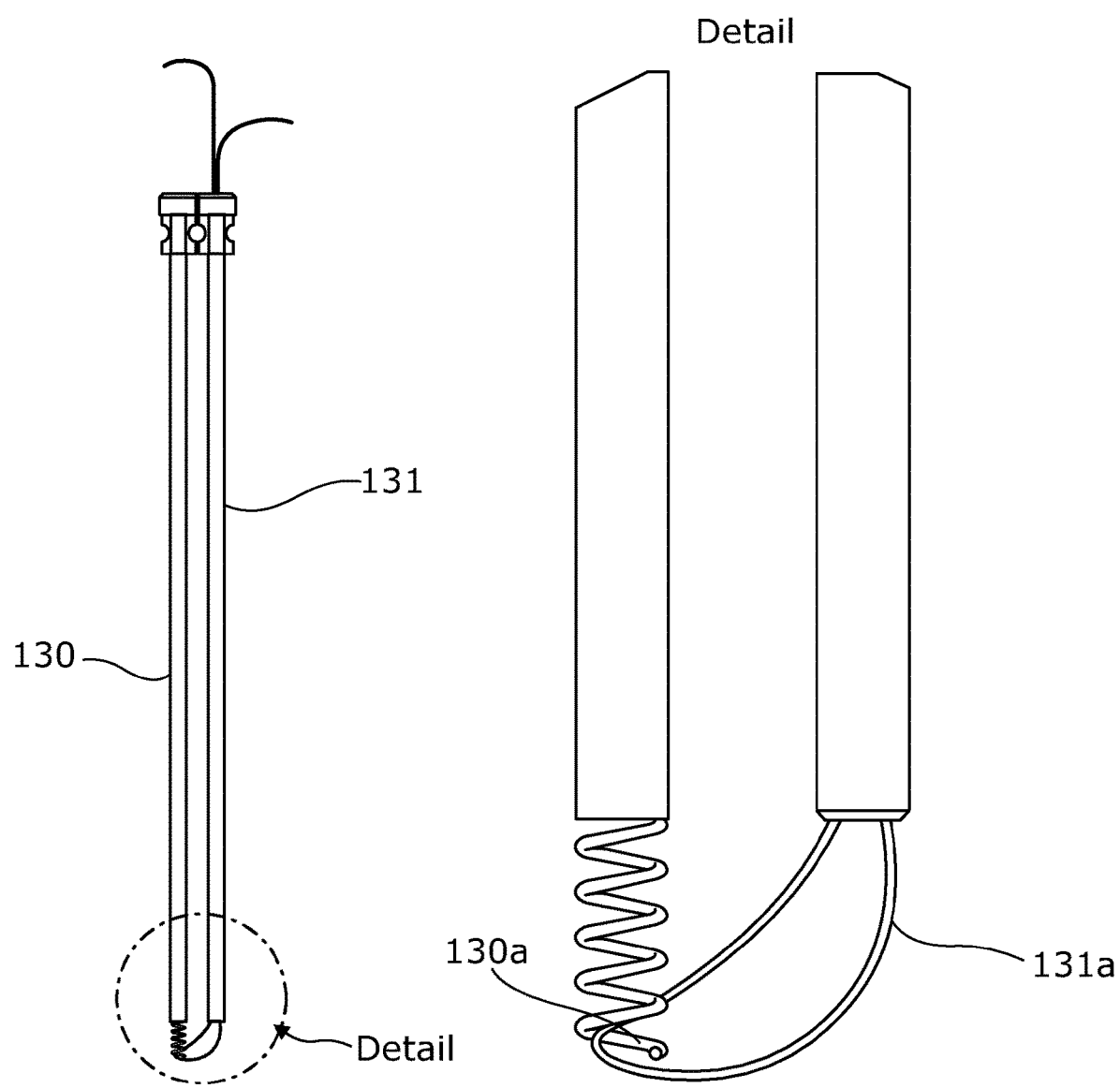
FIG. 8 is a plan view of a wire kit of the invention, including a detail of the ends of the wires

The wire kit of the invention is shown in FIG. 8.

The wire kit comprises a first wire 130 having engagement means on is distal end and a second wire 131 having corresponding engagement means on its distal end.

It can be seen, especially from the detail section of FIG. 8, that the first wire 130 has a hook 130a on its distal end and the second wire has a loop 131a on its distal end. However, alternatives to this could be envisaged. For example, both wires could have a hook at their distal ends, or a magnet-based system could be used to cause engagement.

The dislodger device of the invention is shown in FIG. 9.

The dislodger device has elongate body 51 with a proximal end 51a and a distal end 51b. There is a dislodging portion 52 extending outwardly from the elongate body 51, the dislodging portion being located closer to the distal end of the elongate body than the proximal end of the elongate body e.g. at a distance from the distal end of from 2.5 to 10 mm. The dislodging portion has a curved smooth outer surface 52*a*, with the outer surface having a convex curvature.

Therefore in the event the wire become stuck as it travels up the medial or lateral face of the implant, the dislodging portion can be provided to present its curved surface and the wire can ride over the curved surface.

The invention claimed is:

1. A targeting kit suitable for use in removing an implant, especially a femoral implant, from the surrounding tissue, wherein the targeting kit comprises:
a mounting arrangement for releasably mounting the targeting kit on the head or neck of a femoral implant,
first and second guide members, each of which is an elongate shape with a bore running along its longitudinal axis, each guide member being able to receive a drill bit through its bore,
a holding arrangement for holding the first and second guide members, the holding arrangement being adjustable between a release condition, in which the positions of the first and second guide members are adjustable relative to each other, and a holding condition, in which the first and second guide members are held by the holding arrangement in a fixed position relative to each other,
a bridging arrangement between the mounting arrangement and the first and second guide members, said bridging arrangement being configured to space the first and second guide members with respect to the mounting arrangement, and to permit the mounting arrangement and the first and second guide members to be pivotably adjustable relative to each other, with there being a pivoting movement of the mounting arrangement and the first and second guide members with respect to each other about a pivot point, such that the angle between the mounting arrangement and the first and second guide members can be increased or decreased, with the bridging arrangement being adjustable between a release condition, in which the position of the mounting arrangement is adjustable relative to the first and second guide members, and a holding condition, in which the first and second guide members are fixedly spaced with respect to the mounting arrangement by the bridging arrangement, such that the mounting arrangement can be secured onto the head or neck of the implant, with the first and second guide members being located on the neck or shoulder of the implant, with the first guide member located at the anterior of the implant and the second guide member located at the posterior of the implant, the first guide member being angled such that its longitudinal axis is spaced from and substantially parallel to the anterior surface of the implant and the second guide member being angled such that its longitudinal axis is spaced from and substantially parallel to the posterior surface of the implant.

2. The targeting kit of claim 1, wherein the mounting arrangement for releasably mounting the targeting kit on the head or neck of a femoral implant comprises a clamping component.

3. The targeting kit of claim 2, wherein the clamping component includes an elongate bore within which the neck of the femoral implant can be received.

4. The targeting kit of claim 2, wherein the clamping component has an open configuration, in which it can be placed around the neck of the femoral implant, and a closed configuration, in which it can be clamped shut, with the bore of the clamping component securely receiving and holding the neck of the femoral implant, wherein the clamping component may be locked in this closed configuration.

5. The targeting kit of claim 1, wherein the first and second guide members are slidably adjustable relative to each other, such that the distance between the guide members can be increased or decreased.

6. The targeting kit of claim 1, wherein the first and second guide members are secured to the holding arrangement by the use of first and second securing bores in the holding arrangement that are shaped and sized to receive the guide members.

7. The targeting kit of claim 6, wherein the holding arrangement comprises a body portion that can be located on the shoulder of the implant, wherein the first securing bore is located at a distal end of the body portion and can be located against the anterior surface of the implant when the body portion is located on the shoulder of the implant and the second securing bore is located at a proximal end of the body portion and can be located against the posterior surface of the implant when the body portion is located on the shoulder of the implant, and wherein the distance between the first and second securing bores can be adjusted, set and locked.

8. The targeting kit of claim 7, wherein the body portion has two parts, wherein the first part includes the first of the securing bores and the second part includes the second of the securing bores and wherein the first part and second part of the body portion can be connected together to form the body portion.

9. The targeting kit of claim 8, wherein the body portion comprises an adjustment member that allows the distance between the two parts to be altered.

10. The targeting kit of claim 8, wherein each body part has an interlocking section extending therefrom, wherein each interlocking section has an elongate aperture, such that the two body parts can be fixed at a desired distance to each other by using a fastening member, such as a bolt, to extend through both elongate apertures and fix them together.

11. The targeting kit of claim 8, wherein one body part has an interlocking section extending therefrom, with this interlocking section having an elongate aperture, and the other body part has an interlocking section extending therefrom, with this interlocking section having a fastening member that can extend through the elongate aperture and be secured thereto.

12. The targeting kit of claim 1 wherein the angle between the mounting arrangement and the first and second guide members can be adjusted to be an angle in the range of from 5 degrees to 60 degrees.

13. The targeting kit of claim 12 wherein the angle between the mounting arrangement and the first and second guide members can be adjusted to be an angle in the range of from 30 to 60 degrees.

14. The targeting kit of claim 1, wherein the bridging arrangement includes a ratchet and pinion system to permit the mounting arrangement and the first and second guide members to be pivotably adjustable relative to each other.

15. The targeting kit of claim 1, wherein the pivoting movement of the mounting arrangement and the first and second guide members with respect to each other is about a pivot point which is a ball joint, e.g. a restricted articulation ball joint.

16. The targeting kit of claim 1 wherein:
 (a) a first mounting base connects the bridging arrangement to the mounting arrangement; or
 (b) a first mounting base connects the bridging arrangement to the holding arrangement; or
 (c) a first mounting base connects the bridging arrangement to both the mounting arrangement and the holding arrangement.

17. The targeting kit of claim 1 wherein a first mounting base connects with the holding arrangement at or near the pivot point about which the relative pivotal movement of the mounting arrangement and the first and second guide members occurs.

18. The targeting kit of claim 1 wherein the bridging arrangement includes a locking mechanism for locking the mounting arrangement relative to the first and second guide members.

19. A kit comprising the targeting kit as defined in claim 1 together with one or more of (and in particular three or more of, or four or more of, or all of):
 (a) an extra medullary targeting device that can attach to the first guide member and the second guide member in turn to check their alignment, to check that the guide member in question is pointing to the distal tip of implant, as determined via x-ray;
 (b) an osteotome device that can remove bony ingrowth located adjacent to the anterior access tunnel, and remove bony ingrowth located adjacent to the posterior access tunnel and the posterior surface of the implant;
 (c) a curette device that can remove bony ingrowth located between the implant and the femur in the anterior aspect, and remove bony ingrowth located between the implant and the femur in the posterior aspect;
 (d) a medial-lateral cavity maker device that can remove bony ingrowth located at the distal end of the implant, to create a cavity at the distal end of the implant that extends in the medial and lateral directions;
 (e) a wire delivery device that can provide a wire to extend from a first access point at the proximal surface of the surrounding tissue to a second access point at the proximal surface of the surrounding tissue via the anterior access tunnel, the cavity at the distal end of the implant and the posterior access tunnel, the wire comprising a cutting portion that can be used to cut away bony ingrowth at the surface of the implant; or a medial-lateral clearance device that can remove bony ingrowth located at the antro-lateral edge of the implant, at the antro-medial edge of the implant, at the postro-lateral edge of the implant and at the postro-medial edge of the implant.

* * * * *